(12) United States Patent
Behenna et al.

(10) Patent No.: US 7,235,698 B2
(45) Date of Patent: Jun. 26, 2007

(54) ENANTIOSELECTIVE, CATALYTIC ALLYLATION OF KETONES AND OLEFINS

(75) Inventors: Douglas C. Behenna, Elverson, PA (US); Brian M. Stoltz, Pasadena, CA (US); Justin T. Mohr, Pasadena, CA (US); Andrew M. Harned, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/215,449

(22) Filed: Aug. 29, 2005

(65) Prior Publication Data

US 2006/0084820 A1   Apr. 20, 2006

Related U.S. Application Data

(60) Provisional application No. 60/605,350, filed on Aug. 27, 2004.

(51) Int. Cl.
  *C07C 45/00* (2006.01)
  *C07C 69/66* (2006.01)
(52) U.S. Cl. ............ 568/314; 568/317; 568/346; 568/349; 568/398; 560/174
(58) Field of Classification Search ............. None
  See application file for complete search history.

(56) References Cited

U.S. PATENT DOCUMENTS

| | | | |
|---|---|---|---|
| 4,362,670 A | 12/1982 | Woo | |
| 5,723,652 A | 3/1998 | Minami | |
| 5,955,634 A | 9/1999 | Grosselin et al. | |
| 6,620,954 B1 | 9/2003 | Boaz | |
| 6,673,774 B2 | 1/2004 | Phan et al. | |
| 6,686,428 B2 | 2/2004 | Zhang et al. | |

OTHER PUBLICATIONS

Behenna and Stoltz, "The enantioselective Tsuji allylation," J. Am. Chem. Soc. (2004) 126:15044-15045.
Berkowitz et al., "In situ enzymatic screening (ISES) of P,N-ligands for Ni(0)-mediated asymmetric intramolecular allylic amination," Tetrahedron Asymmetry (2004) 15:2845-2851.
Douglas and Overman, "Catalytic asymmetric synthesis of all-carbon quaternary stereocenters," Proc. Natl. Acad. Sci. USA (2004) 101:5363-5367.
Doyle and Jacobsen, "Enantioselective alkylations of tributyltin enolates catalyzed by Cr(salen)C1: access to enantiomerically enriched all-carbon quaternary centers," J. Am. Chem. Soc. (2005) 125:62-63.
Hallman, "Asymmetric catalysis: ligand design and conformational studies," Thesis, Royal Institute of Technology, Stockholm, Sweden, 2001.
Hayashi et al., "Asymmetric synthesis catalyzed by chiral ferrocenylphosphine-transition metal complexes. 5. Palladium-catalyzed asymmetric allylation of active methine compounds," J. Org. Chem. (1988) 53:113-120.

Kubota and Koga, "Enantioselective palladium catalyzed allylic alkylation with phosphorus-containing $C_2$-symmetric chiral amine ligands," Tetrahedron Lett. (1994) 35:6689-6692.
Kuwano, et al., "Catalytic asymmetric allylation of prochiral nucleophiles, α-acetamido-β-ketoesters," J. Am. Chem. Soc. (1999) 121:3236-3237.
Lennon, "Application of Trost palladium(0) catalyzed asymmetric allylic alkylation technology," Chemistry Today (2004) 22:11-12.
Mermerian and Fu, "Catalytic enantioselective synthesis of quaternary stereocenters via intermolecular C-acylation of silyl ketene acetals: dual activation of the electrophile and the nucleophile," J. Am. Chem. Soc. (2003) 125:4050-4051.
Minami et al., "Reactions of allylic carbonates catalyzed by palladium, rhodium, ruthenium, molybdenum, and nickel complexes: allylation of carbonucleophiles and decarboxylation-dehydrogenation," J. Organometallic Chem. (1985) 296:269-280.
Mohr et al., "The deracemization of quaternary stereocenters by palladium-catalyzed enantioconvergent decarboxylative allylation of racemic β-ketoesters," Angew. Chem. Intl. Ed. (2005) 44:2-6.
Murahashi et al., "Palladium(0)-catalyzed rearrangement of N-allylenamines. Synthesis of δ,ε-unsaturated amines and γ,δ-unsaturated carbonyl compounds," J. Org. Chem. (1988) 53:4489-4495.
Nordstrom et al., "Enantioselective allylic substitutions catalyzed by [(hydroxyalkyl)pyridinooxazoline]- and [(alkoxyalkyl)pyridinooxazoline]palladium complexes," J. Org. Chem. (1997) 62:1604-1609.
Pfaltz and Drury, III, "Design of chiral ligands for asymmetric catalysis: From $C_2$-symmetric P,P- and N,N-ligands to sterically and electronically nonsymmetrical P,N-ligands," Proc. Natl. Acad. Sci. USA (2004) 101:5723-5728.
Satoshi et al., "Catalytic enantioselective allylation of ketones with novel chiral bis-titanium(IV) catalyst," Chirality (2003) 15:68-70.
Sawamura et al., "Chiral phosphine ligands modified by crown ethers: an application to palladium-catalyzed asymmetric allylation of β-diketones," J. Am. Chem. Soc. (1992) 114:2586-2592.
Stephenson, "Organometallic chemistry: The transition elements," Chap. 7, Annual Reports of the Chemical Society, Section B, Organic Chemistry, 93:197-247, 1996.
Sugimoto et al., "Enantioselective allylation of aldehydes with (dialkoxyallyl)chromium(III) complexes," J. Org. Chem. (1997) 62:2322-2323.
Togni et al., "A novel easily accessible chiral ferrocenyldiphosphine for highly enantioselective hydrogenation, allylic alkylation, and hydroboration reactions," J. Am. Chem. Soc. (1994) 116:4062-4066.

(Continued)

*Primary Examiner*—Sikarl A. Witherspoon
(74) *Attorney, Agent, or Firm*—Isaac M. Rutenberg; Dianne E. Reed; Mintz, Levin, Cohn, Ferris, Glovsky and Popeo, PC

(57) ABSTRACT

Compounds containing a substituted or unsubstituted allyl group directly bound to a chiral carbon atom are prepared enantioselectively. Starting reactants are either chiral or achiral, and may or may not contain an attached allyloxycarbonyl group as a substituent. Chiral ligands are employed, along with transition metal catalysts. The methods of the invention are effective in providing enantioconvergent allylation of chiral molecules.

85 Claims, No Drawings

OTHER PUBLICATIONS

Trost et al., "Palladium-catalyzed asymmetric allylic alkylation of α-aryl ketones," Angew. Chem. Intl. Ed. (2002) 41:3492-3495.

Trost et al., "Asymmetric allylation of β-ketoesters," J. Am. Chem. Soc. (1997) 119:7879-7880.

Trost et al., "Pd asymmetric allylic alkylation (AAA). A powerful synthetic tool," Chem. Pharm. Bull. (Tokyo) (2002) 50:1-14.

Trost, "Asymmetric catalysis: an enabling science," Proc. Natl. Acad. Sci. USA (2004) 101:5348-5355.

Trost and Xu, "Regio- and enantioselective Pd-catalyzed allylic alkylation of ketones through allyl enol carbonates," J. Am. Chem. Soc. (2005) 127:2846-2847.

Trost et al., "Palladium-catalyzed asymmetric alkylation of ketone enolates," J. Am. Chem. Soc. (1999) 121:6759-6760.

Tsuji et al., "Palladium-catalyzed allylation of ketones and aldehydes via allyl enol carbonates," Tetrahedron Lett. (1983) 24:1793-1796.

Tsuji et al., "Allylic carbonates. Efficient allylating agents of carbonucleophiles in palladium-catalyzed reactions under neutral conditions," J. Org. Chem. (1985) 50:1523-1529.

Tsuji and Minami, "New synthetic reactions of allyl alkyl carbonates, allyl β-keto carboxylates, and allyl vinylic carbonates catalyzed by palladium complexes," Acc. Chem. Res. (1987) 20:140-145.

Tsuji et al., "Palladium-catalyzed allylation of ketones and akdehydes with allylic carbonates via silyl enol ethers under neutral conditions," Chem. Lett. (1983) 1325-1326.

You et al., "Highly efficient ligands for palladium-catalyzed asymmetric alkylation of ketone enolates," Org. Lett. (2001) 3:149-151.

ENANTIOSELECTIVE, CATALYTIC ALLYLATION OF KETONES AND OLEFINS

CROSS REFERENCE TO RELATED APPLICATION

This application claims priority under 35 U.S.C. § 119(e)(1) to Provisional U.S. Patent Application Ser. No. 60/605,350, filed Aug. 27, 2004, the disclosure of which is incorporated herein by reference in its entirety.

TECHNICAL FIELD

The present invention relates in general to enantioselective allylation reactions. In particular, the invention relates to enantioselective carbon-carbon bond formation reactions, and the methods of the invention are useful in synthetic organic chemistry.

BACKGROUND

Allylic alkylations form an important class of reactions in synthetic organic chemistry (Trost et al. (2002) *Chem. Pharm. Bull.* (Tokyo) 50:1–14; Hayashi et al. (1988) *J. Org. Chem.* 53: 113–120; Trost et al. (1997) *J. Am. Chem. Soc.* 119: 7879–7880; Sugimoto et al. (1997) *J. Org. Chem.* 62: 2322–2323; Satoshi et al, (2003) *Chirality* 15: 68–70). The unique reactivity of compounds containing allylic groups accounts for their utility in synthetic transformations and multi-step syntheses. Although numerous methods exist for adding allyl groups onto compounds displaying a variety of structures and functional groups, current limitations have generated much effort towards expanding the scope of the transformation.

A well-established approach towards allylic alkylation is via simple nucleophilic substitution. Under basic conditions, alcohols, amines and carbanion precursors such as malonates form nucleophiles that react with alkyl halides or triflates to form the corresponding O—, N— or C-alkylated products. As an example of this method, allylic alkylation of these nucleophilic substrates can be achieved using allyl halides. Regio- and stereocontrol over the alkylation product, however, is highly dependent upon the structure of the reactant.

An important subset of allylation reactions in general is the formation of α-allyl ketones. Allylation of allyl-enol carbonates is one approach toward this goal. As originally described (Tsuji et al. (1987) *Acc. Chem. Res.* 20: 140–145; Tsuji et al. (1983) *Tetrahedron Lett.* 24: 1793–1796; Tsuji et al. (1985) *J. Org. Chem.* 50: 1523–1529; Tsuji et al. (1983) *Chem. Lett.* 12: 1325–1326), a palladium catalyst is used in conjunction with a phosphine ligand such as PPh$_3$. The reaction proceeds via decarboxylative degradation of the starting material to form, in situ, an electrophilic allyl moiety and a nucleophilic enolate. The reaction affords excellent regiocontrol, and occurs under essentially neutral conditions. Unfortunately, the allylation reported by Tsuji et al. displays no stereocontrol; the reaction results in a racemic mixture of α-allylcyclohexanone products. As a result of the lack of stereocontrol, this approach has since been used and reported as a synthetic tool only sparingly.

Synthetic methods for preparing α-quaternary carbons are generally more useful when the products are enantioenriched. Enantioselectivity has been achieved in allylation reactions for a limited pool of substrates using a Palladium catalyst in conjunction with chiral ligands. These systems have been essentially confined to allylation of β-diketones and β-ketoesters using prochiral electrophiles, or to α-aryl ketones and cyclic ketones that can only form a single enolate (Hayashi et al. (1988) *J. Org. Chem.* 53: 113–120; Sawamura et al., (1992) *J. Am. Chem. Soc.* 114: 2586–2592; Trost et al. (1997) *J. Am. Chem. Soc.* 119: 7879–7880; Kuwano, et al. (1999) *J. Am. Chem. Soc.* 121: 3236–3237; Trost et al. (1999) *J. Am. Chem. Soc.* 121: 6759–6760; You et al. (2001) *Org. Lett.* 3: 149–151; Trost et al. (2002) *Angew. Chem. Int. Ed.* 41: 3492–3495). In general, strongly basic conditions are required in order to form the reactive enolate intermediate. For example, Trost et al. (2002) describes the allylation of α-aryl ketones using the strongly basic reagents lithium diisoproplyamide or sodium 1,1,1,3,3,3-hexamethyldisilazide. Hayashi et al. described the enantioselective allylation of β-diketones using a palladium catalyst, while Trost et al. (1997) has shown similar results for β-ketoester substrates. Sugimoto et al. used chromium (III) complexes in order to catalyze enantioselective allylation reactions of aldehydes. Titanium(IV) catalysts were used by Satoshi et al. in order to enantioselectively allylate certain ketones.

In light of the limited success in developing enantioselective allylation reactions, there exists a need in the art for a method to prepare highly enantioenriched α-quaternary cycloalkanones and related compounds via enantioselective allylation. Such a method would, optimally, tolerate of a wide variety of functional groups on the substrate, require mild reaction conditions, and employ readily available catalyst/ligand systems. Also desirable is the ability to carry out the reaction on a broad range of structurally distinct compounds. Flexibility in the choice of the catalyst system is also highly desirable.

BRIEF DESCRIPTION OF THE INVENTION

In one embodiment of the invention, a method is provided for synthesizing a compound containing a substituted or unsubstituted allyl group directly bound to a chiral carbon atom. The method comprises contacting an allyloxycarbonyl-substituted reactant with a transition metal catalyst in the presence of a chiral ligand. The allyloxycarbonyl group can be optionally substituted with one or more nonhydrogen substituents.

In a further embodiment of the invention, a method is provided for enantioselectively allylating an olefinic substrate. The method comprises contacting the substrate with an allylating reagent in the presence of a transition metal catalyst and a chiral ligand under reaction conditions effective to provide a compound containing a substituted or unsubstituted allyl group. The substituted or unsubstituted allyl group is directly bound to a chiral carbon atom. The olefinic substrate has the structure of formula (I)

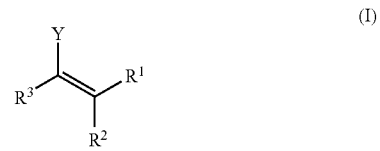

wherein, in formula (I):

R$^1$, R$^2$, and R$^3$ are independently selected from H, hydrocarbyl, substituted hydrocarbyl, heteroatom-containing hydrocarbyl, substituted heteroatom-containing hydrocarbyl, and functional groups, wherein any two of R$^1$, R$^2$, and R$^3$ may be taken together to form a cycle;

Y is selected from —OR$^4$, —NR$^5$R$^6$, and SR$^7$, in which:

R$^4$ is selected from SiR$^8$R$^9$R$^{10}$, SnR$^8$R$^9$R$^{10}$, and BR$^{11}$R$^{12}$, wherein R$^8$, R$^9$, and R$^{10}$ are independently selected from hydrocarbyl and substituted hydrocarbyl, R$^{11}$ and R$^{12}$ are independently selected from hydrocarbyl, substituted hydrocarbyl, heteroatom-containing hydrocarbyl, and substituted heteroatom-containing hydrocarbyl, and can optionally be taken together to form a cycle;

R$^5$ and R$^6$ are independently selected from Mg, Li, Zn, hydrocarbyl, substituted hydrocarbyl, heteroatom-containing hydrocarbyl, and substituted heteroatom-containing hydrocarbyl, and R$^5$ and R$^6$ can optionally be taken together to form a cycle; and R$^7$ is hydrogen or hydrocarbyl.

In a further embodiment of the reaction, a method is provided for the catalytic enantioconvergent synthesis of compounds containing a quaternary stereocenter from a mixture of stereoisomers. The method comprises contacting the mixture with a transition metal catalyst in the presence of a chiral ligand under reaction conditions sufficient to provide for enantioselective formation of an allyl-substituted stereocenter.

DETAILED DESCRIPTION OF THE INVENTION

Definitions and Nomenclature

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

Where lists are used to identify multiple embodiments, it is understood that modifiers stated at the beginning of the list apply to each element in the list. Thus, for example, in a list of "chiral compounds", each compound in the list is understood to be chiral.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a functional group" includes a single functional group as well as two or more functional groups that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched or cyclic saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, preferably 1 to 4 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkenyl" as used herein refers to a linear, branched or cyclic hydrocarbon group of 2 to 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of 2 to 6 carbon atoms, preferably 2 to 4 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Preferred alkynyl groups herein contain 2 to 12 carbon atoms. The term "lower alkynyl" intends an alkynyl group of 2 to 6 carbon atoms, preferably 2 to 4 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, preferably 1 to 4 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl,
—O(CO)-aryl, or —O(CO)-aralkyl, wherein "alkyl," "aryl, and "aralkyl" are as defined above.

The term "cyclic" refers to alicyclic or aromatic substituents that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{24}$ aryloxy, acyl (including $C_2$–$C_{24}$ alkylcarbonyl (—CO-alkyl) and $C_6$–$C_{24}$ arylcarbonyl (—CO-aryl)), acyloxy (—O-acyl), $C_2$–$C_{24}$ alkoxycarbonyl (—(CO)—O-alkyl), $C_6$–$C_{24}$ aryloxycarbonyl (—(CO)—O-aryl), halocarbonyl (—CO)—X where X is halo), $C_2$–$C_{24}$ alkylcarbonato (—O—(CO)—O-alkyl), $C_6$–$C_{24}$ arylcarbonato (—O—(CO)—O-aryl), carboxy (—COOH), carboxylato (—COO$^-$), carbamoyl (—(CO)—NH$_2$), mono-($C_1$–$C_{24}$ alkyl)-substituted carbamoyl (—(CO)—NH($C_1$–$C_{24}$ alkyl)), di-($C_1$–$C_{24}$ alkyl)-substituted carbamoyl (—(CO)—N($C_1$–$C_{24}$ alkyl)$_2$), mono-($C_6$–$C_{24}$ aryl)-substituted carbamoyl (—(CO)—NH-aryl), di-($C_6$–$C_{24}$ aryl)-substituted carbamoyl (—(CO)—N(aryl)$_2$), di-N—($C_1$–$C_{24}$ alkyl), N—($C_6$–$C_{24}$ aryl)-substituted carbamoyl, thiocarbamoyl (—(CS)—NH$_2$), carbamido (—NH—(CO)—NH$_2$), cyano(-C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, $C_2$–$C_{24}$ alkylamido (—NH—(CO)-alkyl), $C_6$–$C_{24}$ arylamido (—NH—(CO)-aryl), imino (—CR=NH where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), alkylimino (—CR=N(alkyl), where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), arylimino (—CR=N(aryl), where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), nitro (—NO$_2$), nitroso (—NO), sulfo (—SO$_2$—OH), sulfonato (—SO$_2$—O$^-$), $C_1$–$C_{24}$ alkylsulfanyl (—S-alkyl; also termed "alkylthio"), arylsulfanyl (—S-aryl; also termed "arylthio"), $C_1$–$C_{24}$ alkylsulfinyl (—(SO)-alkyl), $C_5$–$C_{24}$ arylsulfinyl (—(SO)-aryl), $C_1$–$C_{24}$ alkylsulfonyl (—SO$_2$-alkyl), $C_5$–$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$–$C_{24}$ alkyl (preferably $C_1$–$C_{12}$ alkyl, more preferably $C_1$–$C_6$ alkyl), $C_2$–$C_{24}$ alkenyl (preferably $C_2$–$C_{13}$ alkenyl, more preferably $C_2$–$C_6$ alkenyl), $C_2$–$C_{24}$ alkynyl (preferably $C_2$–$C_{12}$ alkynyl, more preferably $C_2$–$C_6$ alkynyl), $C_5$–$C_{24}$ aryl (preferably $C_5$–$C_{14}$ aryl), $C_6$–$C_{24}$ alkaryl (preferably $C_6$–$C_{16}$ alkaryl), and $C_6$–$C_{24}$ aralkyl (preferably $C_6$–$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

The terms "enantiomer excess," "enantiomeric excess," and "e.e." are used interchangeably and are defined as |F(+)−F(−)| for a mixture of (+)- and (−)-enantiomers, with composition given as the mole or weight fractions F(+) and F(−), such that F(+)+F(−)=1. When given as a percentage, enantiomer excess is defined by 100*|F(+)−F(−)|.

The terms "racemate," "racemic form," and "racemic mixture" are used interchangeably to refer to a substantially equimolar mixture of two enantiomers, and can be designated using the (±) symbol.

II. Reactants

A preferred embodiment of the invention is a method for synthesizing a compound containing a substituted or unsubstituted allyl group directly bound to a chiral carbon atom, comprising contacting an allyloxycarbonyl-substituted reactant with a transition metal catalyst in the presence of a chiral ligand. The allyloxycarbonyl-substituted reactant can be achiral or chiral. When the reactant is chiral, the reactant can be present as a racemic mixture, or the reactant can be substantially enantiopure. Preferably, the method is enantioselective, such that the compound is provided in enantioenriched form.

The allyloxycarbonyl group is optionally substituted with one or more nonhydrogen substituents, such that the allyloxycarbonyl group has the structure of formula (II)

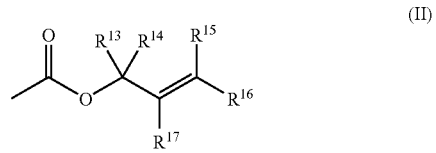

wherein $R^{13}$, $R^{14}$, $R^{15}$, $R^{16}$ and $R^{17}$ are independently selected from H, hydrocarbyl, substituted hydrocarbyl, heteroatom-containing hydrocarbyl, substituted heteroatom-containing hydrocarbyl, and functional groups, and any two of $R^{13}$, $R^{14}$, $R^{15}$, $R^{16}$ and $R^{17}$, may be taken together and/or linked to another atom within the reactant to form a cyclic group.

Furthermore, the allyloxycarbonyl-substituted reactant can be cyclic or acyclic. Preferred reactants include without limitation allyl enol carbonates, β-ketoesters, and compounds wherein the allyloxycarbonyl group is directly bound to a carbon atom that is additionally substituted with an electron withdrawing group. Suitable electron withdrawing groups include without limitation nitro, carbonyl, cyano, sulfonato, halo (i.e., Cl, F, Br or I) and halogenated alkyl (typically fluorinated alkyl, preferably perfluorinated lower alkyl such as trifluoromethyl).

A further embodiment of the invention is a method for enantioselectively allylating an olefinic substrate. The method comprises contacting the substrate with an allylating reagent in the presence of a transition metal catalyst and a chiral ligand under reaction conditions effective to provide a compound containing a substituted or unsubstituted allyl group. The substituted or unsubstituted allyl group is directly bound to a chiral carbon atom. The olefinic substrate has the structure of formula (I)

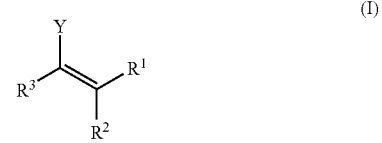

wherein, in formula (I):

$R^1$, $R^2$, and $R^3$ are independently selected from H, hydrocarbyl, substituted hydrocarbyl, heteroatom-containing hydrocarbyl, substituted heteroatom-containing hydrocarbyl, and functional groups, wherein any two of $R^1$, $R^2$, and $R^3$ may be taken together to form a cycle;

Y is selected from —$OR^4$, —$NR^5R^6$, and $SR^7$, in which:

$R^4$ is selected from $SiR^8R^9R^{10}$, $SnR^8R^9R^{10}$, and $BR^{11}R^{12}$, wherein $R^8$, $R^9$, and $R^{10}$ are independently selected from hydrocarbyl and substituted hydrocarbyl, $R^{11}$ and $R^{12}$ are independently selected from hydrocarbyl, substituted hydrocarbyl, heteroatom-containing hydrocarbyl, and substituted heteroatom-containing hydrocarbyl, and can optionally be taken together to form a cycle;

$R^5$ and $R^6$ are independently selected from Mg, Li, Zn, hydrocarbyl, substituted hydrocarbyl, heteroatom-containing hydrocarbyl, and substituted heteroatom-containing hydrocarbyl, and $R^5$ and $R^6$ can optionally be taken together to form a cycle; and $R^7$ is hydrogen or hydrocarbyl.

Preferred substrates that have the structure of formula (I) include, but are not limited to, enol ethers, enamines, boranes, lactams, lactones, and ketene acetals.

When Y is —$OR^4$ in formula (I), the olefinic substrate is an enol ether. When $R^4$ is $SiR^8R^9R^{10}$, wherein $R^8$, $R^9$, and $R^{10}$ are as defined previously, the substrate is a silyl enol ether, and a desilylating reagent is necessary to act as an activator. Suitable desilylating agents include without limitation MeLi, NaOEt, KOEt, KOtBu, CsF, LiOMe, tetrabutylammonium difluorotriphenylsilicate (TBAT), tetrabutylammonium fluoride (TBAF), and any of the reagents disclosed in U.S. Pat. No. 5,821,362 to Kaneko et al.

When Y is —$NR^5R^6$ in formula (I), the olefinic substrate is an enamine. Products from the methods of the invention using enamines as substrate are generally iminium ions. One of ordinary skill in the art would appreciate that such iminium ions can be converted to ketones via hydrolysis, with water being the most preferred hydrolyzing agent.

Generally, the allylating agent has the structure of formula (III)

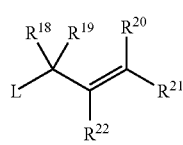

wherein, in formula (III), L is a leaving group, and $R^{18}$, $R^{19}$, $R^{20}$, $R^{21}$ and $R^{22}$ independently selected from H, hydrocarbyl, substituted hydrocarbyl, heteroatom-containing hydrocarbyl, and substituted heteroatom-containing hydrocarbyl. Any two of $R^{18}$, $R^{19}$, $R^{20}$, $R^{21}$ and $R^{22}$ may be taken together to form a cycle, and any of $R^{18}$, $R^{19}$, $R^{20}$, $R^{21}$ and $R^{22}$ may further connect to L to form a cycle.

Suitable leaving groups for L include, without limitation, halo, substituted or unsubstituted alkoxy, substituted or unsubstituted amido, substituted or unsubstituted sulfide, substituted or unsubstituted carbamato, and substituted or unsubstituted carbonato.

Therefore, allylating agents that conform to formula (III) include by way of example and not limitation allyl alcohols, allyl esters, allyl amides, allyl ureas, allyl carbamates, allyl halides, and allyl carbonates. Preferred examples include substituted and unsubstituted forms of allyl acetate, allyl triflate, allyl tosylate, allyl isocyanate, allyl isothiocyanate, allyl bromide, allyl chloride, allyl iodide, 3-chlorocyclohexene, 3-chlorocyclopentene, 3-bromocyclohexene, 3-bromocyclopentene, 3-iodocyclohexene, 3-iodocyclopentene, bis(allyl)carbonate, allyl methyl carbonate, allyl phenyl carbonate, allyl ethyl carbonate, allyl 1-benzotriazolyl carbonate, and allyl chlorophenyl carbonate.

Product compounds generated by the reactions of the invention comprise an allyl moiety that is covalently attached to the compound via a newly-formed carbon-carbon bond. Due to the catalytic nature of the allylation reactions of the invention, as well as the presence of chiral ligands in the reactions, the products are enantioenriched such that one stereoisomer of the product is present in greater abundance than all others. In a preferred embodiment, the enantiomeric excess of the product from the reaction is at least 60%, with an enantiomeric excess of at least 75% being more preferred, and an enantiomeric excess of at least 85% being most preferred. Determination of enantiomeric excess of the product can be via any of a number of methods that are well-documented and appreciated by one of skill in the art. Products from the methods of the invention include, without limitation, α-allyl ketones, α-cyclohexenyl ketones, poly(butadiene)s, and iminium ions.

III. Catalysts

The reactions of the invention are carried out catalytically. For catalytic purposes, a compound which we describe as a "catalyst" is provided, and a chiral ligand is also provided. The chiral ligand may be provided separately from the catalyst or as a part of it. The term "catalyst," for purposes of this patent application, therefore has a meaning somewhat broader than its ordinary meaning, in that it also encompasses compounds which achieve a catalytic effect in conjunction with or after having reacted with a chiral ligand (and, in certain cases discussed below, also after having reacted with a nucleophilic reagent). Preferred catalysts are complexes of transition metals. Many such catalysts may be purchased from commercial sources, or may be prepared prior to their use using published procedures and standard literature methods.

Preferred catalysts for the reactions of the invention are complexes of transition metals wherein the metal is selected from Groups 6, 8, 9 and 10 in the periodic table. More preferred is the group of transition metals that includes molybdenum, tungsten, iridium, rhenium, ruthenium, nickel, platinum, and palladium. Most preferred are complexes of palladium.

Preferred catalysts comprise complexes of electrically neutral transition metals. In one embodiment of the invention, a complex of a neutral transition metal is employed directly in the reaction. It should be appreciated that the air and moisture sensitivity of many complexes of neutral transition metals will necessitate appropriate handling precautions. This may include the following precautions without limitation: minimizing exposure of the reactants to air and water prior to reaction; maintaining an inert atmosphere within the reaction vessel; properly purifying all reagents; and removing water from reaction vessels prior to use.

Exemplary neutral transition metal catalysts include, without limitation, $Mo(CO)_6$, $Mo(MeCN)_3(CO)_3$, $W(CO)_6$, $W(MeCN)_3(CO)_3$, $[Ir(1,5\text{-cyclooctadiene})Cl]_2$, $[Ir(1,5\text{-cyclooctadiene})Cl]_2$, $[Ir(1,5\text{-cyclooctadiene})Cl]_2$, $Rh(PPh_3)_3Cl$, $[Rh(1,5\text{-cyclooctadiene})Cl]_2$, $Ru(\text{pentamethylcyclopentadienyl})(MeCN)_3PF_6$, $Ni(1,5\text{-cyclooctadiene})_2$, $Ni[P(OEt)_3]_4$, tris(dibenzylideneacetone)dipalladium(0), tris(dibenzylideneacetone)dipalladium(0)-chloroform adduct, $Pd(OC(=O)CH_3)_2$, $Pd(3,5\text{-dimethyoxy-dibenzylideneacetone})_2$, $PdCl_2(R^{23}CN)_2$; $PdCl_2(PR^{24}R^{25}R^{26})_2$; $[Pd(\eta^3\text{-allyl})Cl]_2$; and $Pd(PR^{24}R^{25}R^{26})_4$, wherein $R^{23}$, $R^{24}$, $R^{25}$, and $R^{26}$ are independently selected from H, hydrocarbyl, substituted hydrocarbyl, heteroatom-containing hydrocarbyl, and substituted heteroatom-containing hydrocarbyl. The transition metal catalysts tris(dibenzylideneacetone)dipalladium(0) is most preferred.

To improve the effectiveness of the catalysts discussed herein, additional reagents may be employed as needed, including, without limitation, salts, solvents, and other small molecules. Preferred additives include $AgBF_4$, $AgOSO_2CF_3$, $AgOC(=O)CH_3$, $PPh_3$, $P(n\text{-}Bu)_3$, and bipyridine. These additives are preferably used in an amount that is in the range of about 1 equivalent to about 5 equivalents relative to the amount of the catalyst.

The neutral oxidation state of the transition metal can also be obtained in situ, by the reduction of transition metal complexes that are initially in a higher oxidation level. An exemplary method for reduction of the transition metal complex is with the use of nucleophilic reagents including, without limitation, NBu$_4$OH, tetrabutylammonium difluorotriphenylsilicate (TBAT), tetrabutylammonium fluoride (TBAF), 4-dimethylaminopyridine (DMAP), NMe$_4$OH (H$_2$O)$_5$, KOH/1,4,7,10,13,16-Hexaoxacyclooctadecane, EtONa, TBAT/Trimethyl-(2-methyl-cyclohex-1-enyloxy)-silane, and mixtures thereof. When a nucleophilic reagent is needed for the reduction of the metal complex, the nucleophilic reagent is used in an amount in the range of about 1 mol % to about 20 mol % relative to the reactant, more preferably in the range of about 1 mol % to about 10 mol % relative to the substrate, and most preferably in the range of about 5 mol % to about 8 mol % relative to the substrate.

Exemplary transition metal complexes with a +2 oxidation state include, without limitation, allylchloro[1,3-bis(2, 6-di-i-propylphenyl)imidazol-2-ylidene]palladium (II), ([2S,3S]-bis[diphenylphosphino]butane)($\eta^3$-allyl)palladium (II) perchlorate, [S]-4-tert-butyl-2-(2-diphenylphosphanyl-phenyl)-4,5-dihydro-oxazole($\eta^3$-allyl)palladium(II) hexafluorophosphate (i.e., [Pd(S-tBu-PHOX)(allyl)]PF$_6$), and cyclopentadienyl($\eta^3$-allyl)palladium(II), with [Pd(s-tBu-PHOX)(allyl)]PF$_6$ and cyclopentadienyl($\eta^3$-allyl)palladium(II) being most preferred.

The amount of catalyst to be used in the reactions of the invention is generally measured in relation to the amount of substrate that is present. For the reactions of the invention, the metal from the catalyst is present in an amount ranging from about 1 mol % to about 20 mol % relative to the substrate. More preferably, the metal from the catalyst is present in an amount ranging from about 1 mol % to about 10 mol % relative to the substrate. By "metal from the catalyst" is meant the equivalents (relative to the substrate) of transition metal atoms. Thus, for example, 5 mol % of tris(dibenzylideneacetone)dipalladium(0) provides 10 mol % of metal atoms relative to the substrate.

IV. Ligands

A key feature of the invention is the enantioselectivity of the methods. Enantioselectivity is a result of the presence of chiral ligands during the reactions. Without being bound by theory, enantioselectivity results from the asymmetric environment that is created around the metal center by the presence of chiral ligands. The chiral ligand forms a complex with the transition metal, thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the allylation reactions of the present invention.

Once coordinated to the transition metal center, the chiral ligand influences the orientation of other molecules as they interact with the transition metal catalyst. Coordination of the metal center with a π-allyl group, and reaction of the substrate with the π-allyl-metal complex are dictated by the presence of the chiral ligand. The orientation of the reacting species determines the stereochemistry of the products.

Many factors determine the ability of the chiral ligand to influence the orientation of the reacting species, and thereby determine the stereochemistry of the products. For example, shape and size (i.e., sterics), denticity (mono- or bidentate), and electronic properties affect the ligand-metal complex as well as the interaction of the metal-ligand complex with the nucleophile. These factors can vary substantially between ligands, resulting in correspondingly large differences in the success of the ligands as promoters of enantioselective allylation. For any given substrate, some ligands might provide relatively high product yield, while other ligands affect relatively high enantiopurity of the product. Still other ligands may provide both high yield and high enantiopurity, while still other ligands might provide neither. It should be understood that proper ligand selection for any given substrate will influence the products of the reaction.

Generally, the chiral ligand must be present in an amount in the range of about 0.75 equivalents to about 10 equivalents relative to the amount of metal from the catalyst, preferably in the range of about 0.75 to about 5 equivalents relative to the amount of metal from the catalyst, and most preferably in the range of about 0.75 to about 1.25 equivalents relative to the amount of metal from the catalyst. Alternatively, the amount of the chiral ligand can be measured relative to the amount of the substrate. Then, the chiral ligand is present in an amount ranging from about 1 mol % to about 20 mol %, more preferably from about 2.5 mol % to about 13 mol % relative to the substrate.

Preferred chiral ligands are bidentate, although monodentate ligands and ligands with higher denticity (i.e., tridentate, tetradentate, etc.) can be used in the reactions of the invention. Preferably, the ligand will be substantially enantiopure. By "enantiopure" is meant that only a single enantiomer is present. In many cases, substantially enantiopure ligands can be purchased from commercial sources.

Preferred chiral ligands are those with the structure of formula (IV)

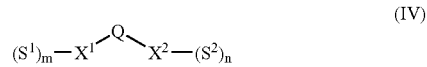

(IV)

wherein, in formula (IV):

Q is a linker selected from hydrocarbylene, substituted hydrocarbylene, heteroatom-containing hydrocarbylene, substituted heteroatom-containing hydrocarbylene, and a coordinated transition metal, and further wherein two or more substituents on Q may be linked to form a cycle;

X$^1$ and X$^2$ are independently selected from P, N, O, S, and As;

m and n are independently selected from 2, 3 and 4, and are chosen to satisfy the valency requirements of X$^1$ and X$^2$, respectively; and S$^1$ and S$^2$ are independently selected from hydrocarbyl, substituted hydrocarbyl, heteroatom-containing hydrocarbyl, and substituted heteroatom-containing hydrocarbyl, wherein two or more substituents on S$^1$ and/or S$^2$ may be linked to form a cycle, and further wherein S$^1$ and/or S$^2$ may form cycles such that X$^1$ and/or X$^2$ are incorporated into heterocycles.

More preferred are chiral ligands selected from oxazoles, phosphinooxazolines, imidazoles, phosphinoimidazolines, phosphines, N-hetero carbenes, N-heterocyclic carbenes, phosphinopyridines, and phosphinoamines. In a preferred embodiment of the invention, the chiral ligand has the structure of formula (V)

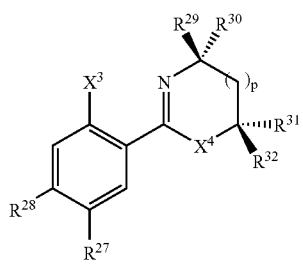

wherein, in formula (V):

$R^{27}$, $R^{28}$, $R^{29}$, $R^{30}$, $R^{31}$, and $R^{32}$ are independently selected from H, hydrocarbyl, substituted hydrocarbyl, heteroatom-containing hydrocarbyl, substituted heteroatom-containing hydrocarbyl, and functional groups, and any two of $R^{27}$, $R^{28}$, $R^{29}$, $R^{30}$, $R^{31}$, and $R^{32}$ on adjacent atoms may be taken together to form a cycle;

$X^3$ is selected from —P(O)$R^{33}R^{34}$, —P$R^{33}R^{34}$, —N$R^{33}R^{34}$, —O$R^{33}$, —S$R^{33}$, and —As$R^{33}R^{34}$, wherein $R^{33}$ and $R^{34}$ are independently selected from H, hydrocarbyl, substituted hydrocarbyl, heteroatom-containing hydrocarbyl, substituted heteroatom-containing hydrocarbyl, and functional groups;

$X^4$ is selected from N$R^{35}$ and O, wherein $R^{35}$ is selected from H, hydrocarbyl, substituted hydrocarbyl, heteroatom-containing hydrocarbyl, substituted heteroatom-containing hydrocarbyl, and functional groups; and p is 0 or 1.

Representative examples of chiral ligands with a structure corresponding to formula (V) include, without limitation, the following structures.

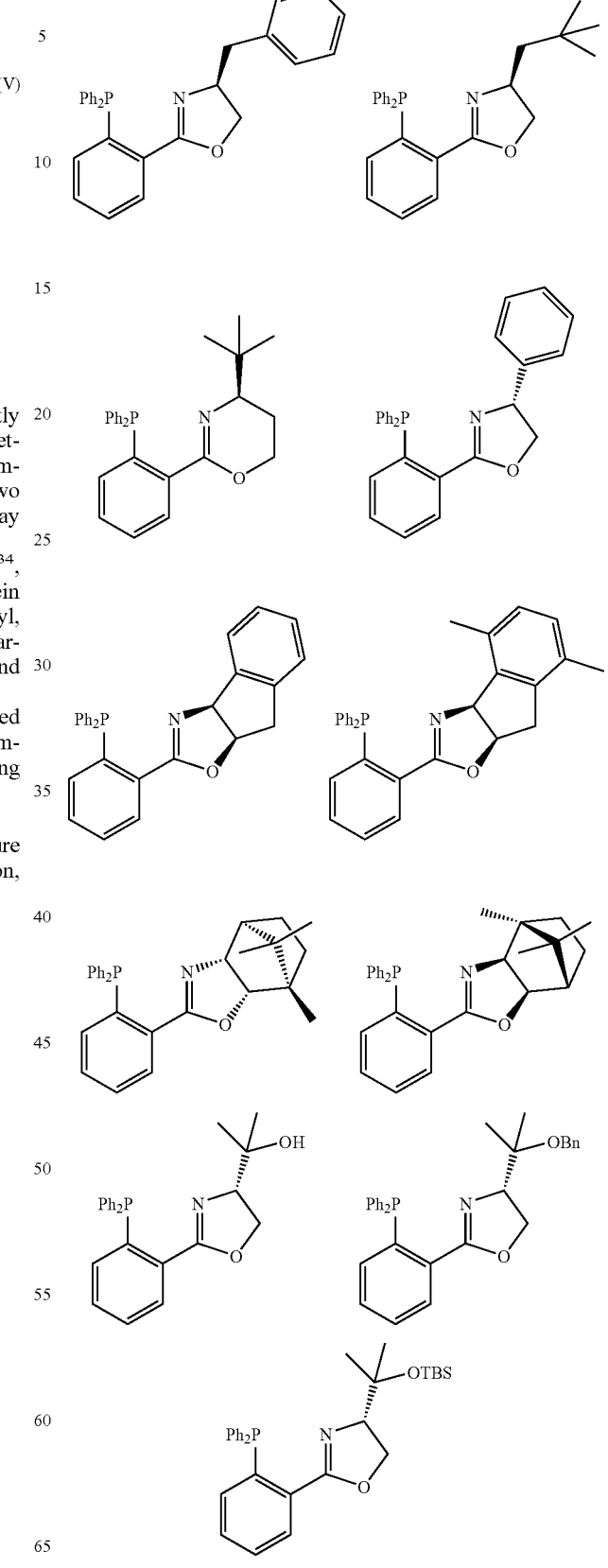

-continued

-continued
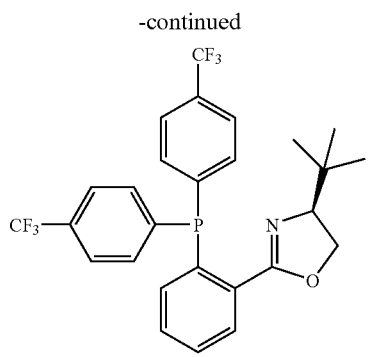
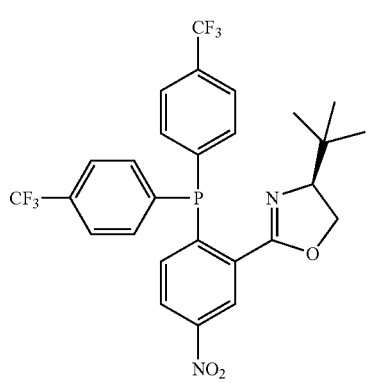
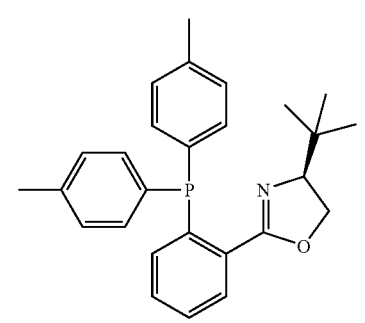
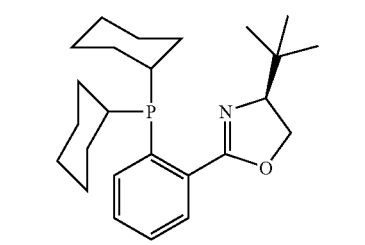
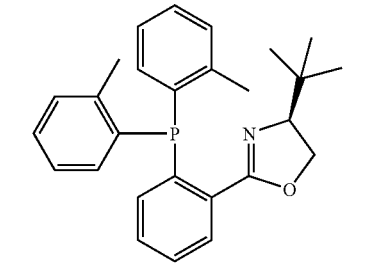
-continued
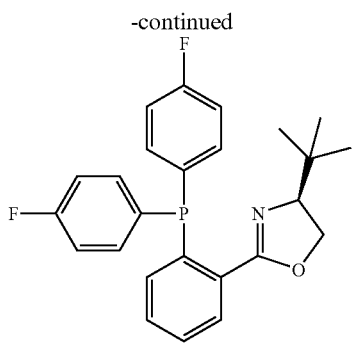
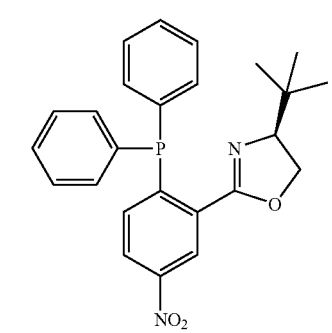
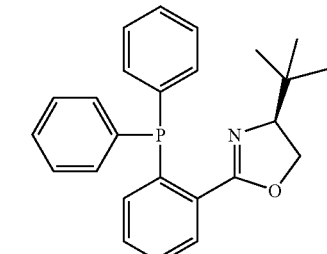
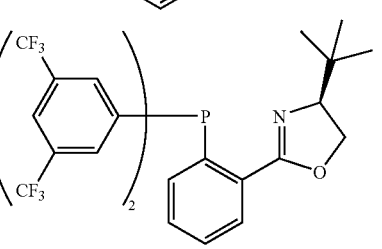
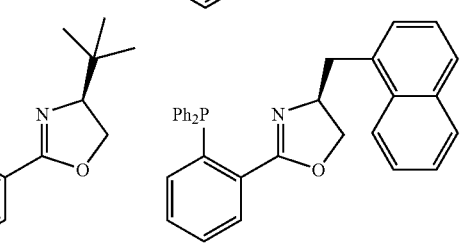
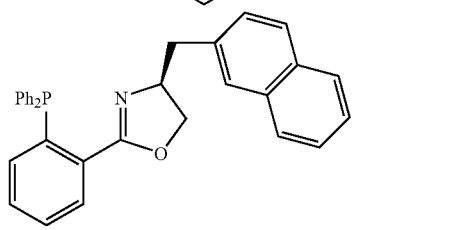

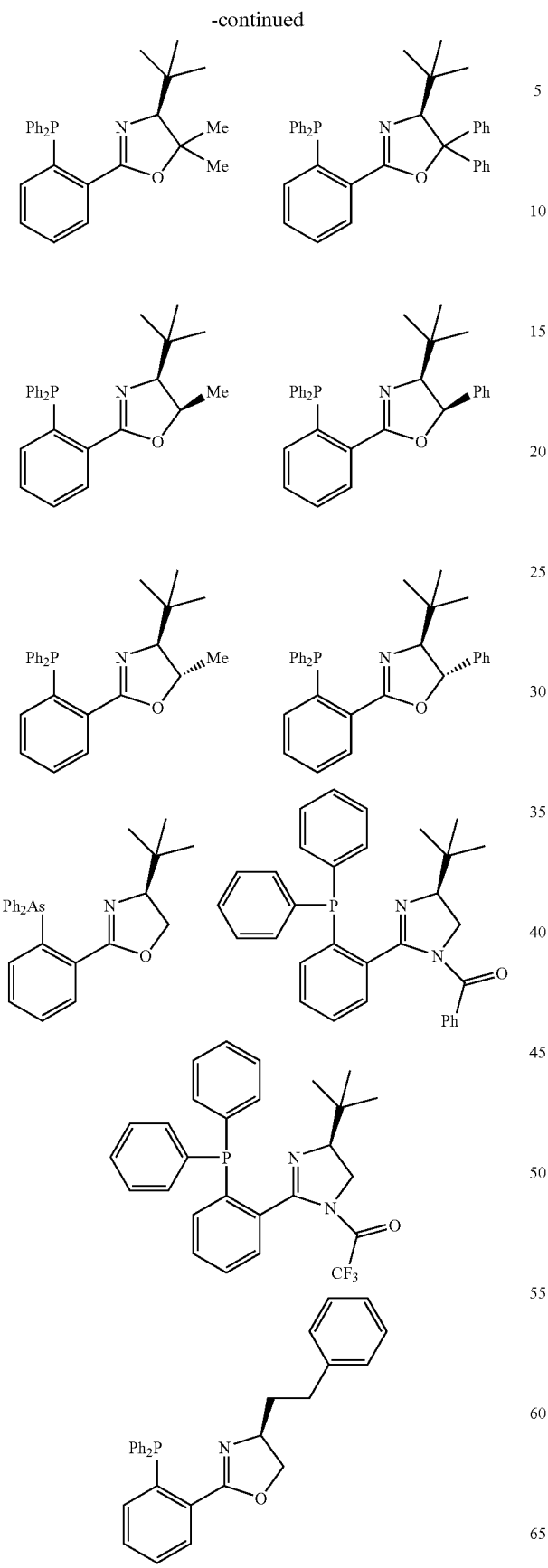
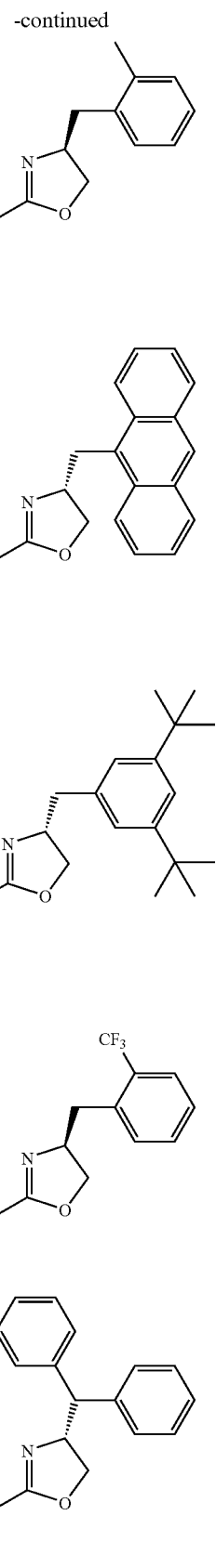

-continued
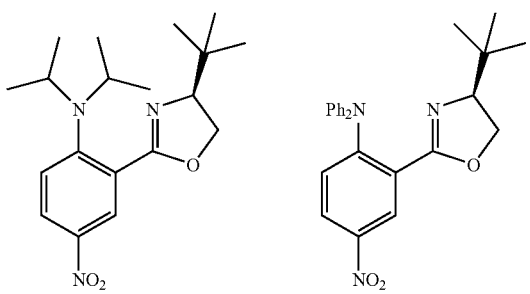
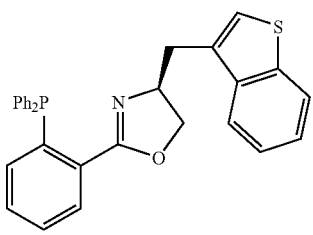
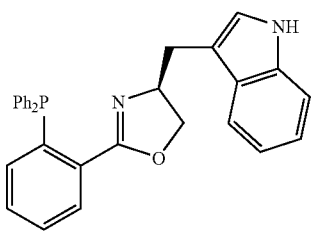
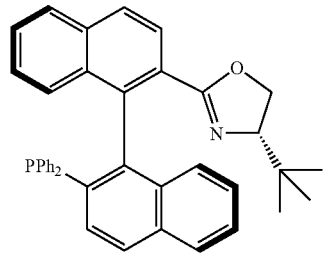
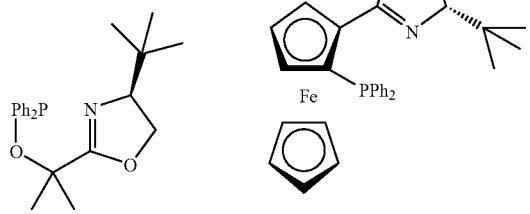
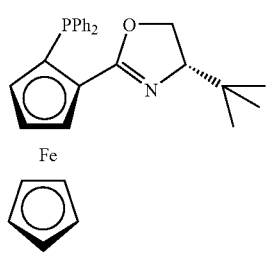
In addition to compounds that have a structure according to formula (V), examples of chiral phosphinooxazolines that are preferred also include the following compounds.
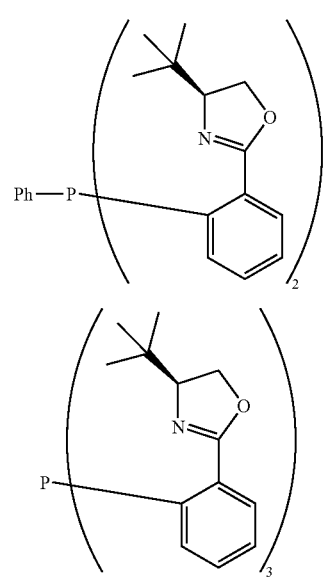
Also preferred are chiral phosphinoamines, bis(phosphines), phosphinopyridines, and N-heterocyclic carbenes, examples of which include the following compounds.
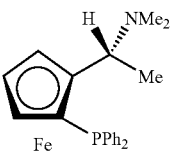 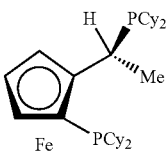
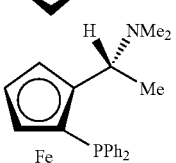

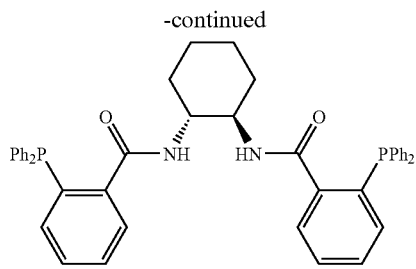
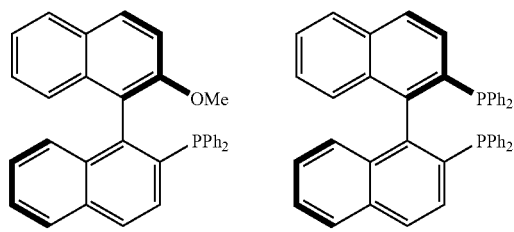
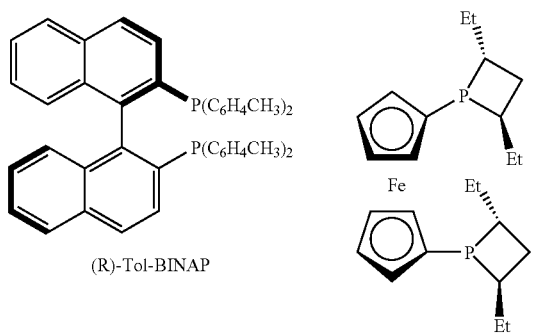
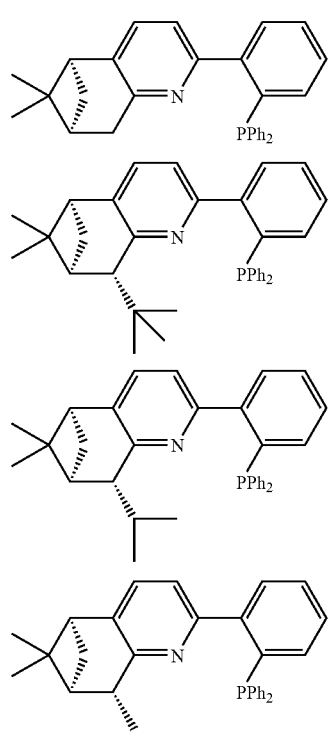

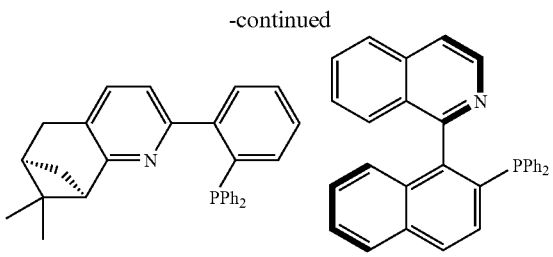
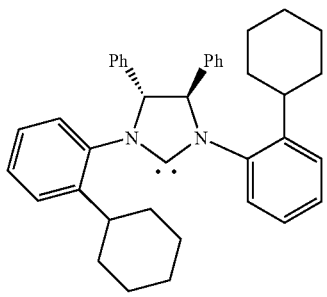
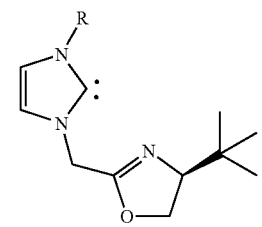

Most preferred are the PHOX-type chiral ligands (R)-2-[2-(diphenylphosphino)phenyl]-4-isopropyl-2-oxazoline, (R)-2-[2-(diphenylphosphino)phenyl]-4-phenyl-2-oxazoline, (S)-2-[2-(diphenylphosphino)phenyl]-4-benzyl-2-oxazoline, and (S)-2-[2-(diphenylphosphino)phenyl]-4-tert-butyl-2-oxazoline.

V. Reaction Conditions

The reactions of the invention are carried out in solvent under an inert atmosphere. Appropriate solvents include without limitation, hydrocarbons, substituted hydrocarbons, heteroatom-containing hydrocarbons, and substituted heteroatom-containing hydrocarbons. Preferred solvents include ethers, amines, ketones, aromatic hydrocarbons, heteroatom-containing aromatic hydrocarbons, and substituted aromatic hydrocarbons. Examples of preferred solvents include 1,4-dioxane, tetrahydrofuran, methyl-tert-butyl ether, diethyl ether, toluene, benzene, diisopropyl ether, ethyl acetate, triethylamine, anisole, acetone, fluorobenzene, and diglyme. Supercritical fluids can also be used as solvents, with carbon dioxide representing one such solvent. Reaction temperatures range from 0° C. to 100° C., with 20° C. to 60° C. being preferred, and 20° C. to 25° C. (i.e., room temperature) being particularly preferred. The reaction time will generally be in the range of 1 hour to 24 hours. Pressures range from atmospheric to pressures typically used in conjunction with supercritical fluids, with the preferred pressure being atmospheric.

VI. Enantioconvergent Syntheses

The methods of the invention are useful in the enantioconvergent synthesis of quaternary stereocenters from racemates bearing quaternary stereocenters.

Preferred substrates for this application include racemic mixtures of compounds that contain a quaternary stereocenter, wherein one of the substitutents on the stereocenter is an allyl carbonate or allyl ester. An example is a mixture consisting essentially of stereoisomers of a β-ketoester. The enantiopurity of the mixture is catalytically increased by contacting the mixture with a transition metal catalyst in the presence of a chiral ligand under reaction conditions sufficient to provide formation of a chiral α-allyl ketone. The catalysts, chiral ligands, and reaction conditions disclosed herein are suitable to affect this transformation.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

Experimental

Materials and Methods: Unless otherwise stated, reactions were performed in flame-dried glassware under an argon atmosphere using dry, deoxygenated solvents. Solvents were dried by passage through an activated alumina column under argon. Tetrabutylammonium difluorotriphenylsilicate (TBAT) was purchased from Sigma-Aldrich Chemical Company and azeotropically dried five times from acetonitrile prior to use. Trimethylsilyl chloride (TMSCl) and triethyl amine (TEA) were distilled from sodium hydride immediately prior to use. Sodium iodide was dried by heating at 90° C. (2 torr) for 12 h. (R,R)-Trost Ligand (3), (R)-BINAP (4), (R,R)-Me-DUPHOS (5), (R,R)-DIOP (6), (R)-MOP (7), (R)-QUINAP (8), (R)-i-Pr-PHOX (11), and Tris(dibenzylideneacetone)dipalladium(0) (Pd$_2$(dba)$_3$) were purchased from Strem and stored in a glove box until immediately before use. (R)-Ph-PHOX (9), (S)-Bn-PHOX (10), and (S)-t-Bu-PHOX (12) were prepared according to Peer et al., *Tetrahedron* 1996, 52, 7547–7583. Allyl chloroformate, diallyl carbonate and dimethallyl carbonate were used as received. Methallyl chloroformate was prepared by the method of Kirby et al., *J. Chem. Soc., Perkin Trans.* 1 1985, 9, 1961–1966. Reaction temperatures were controlled by an IKAmag temperature modulator. Thin-layer chromatography (TLC) was performed using E. Merck silica gel 60 F254 precoated plates (0.25 mm) and visualized by ultraviolet fluorescence quenching, anisaldehyde, or CAM staining. ICN Silica gel (particle size 0.032–0.063 mm) was used for flash chromatography. Analytical chiral HPLC was performed with an Agilent 1100 Series HPLC utilizing chiralcel AD, OD-H, or OJ columns (4.6 mm×25 cm) obtained from Daicel Chemical Industries, Ltd with visualization at 254 nm. Analytical chiral GC was performed with an Agilent 6850 GC utilizing a G-TA (30 m×0.25 cm) column (1.0 mL/min carrier gas flow). Analytical achiral GC was performed with an Agilent 6850 GC utilizing a DB-WAX (30m×0.25 mm) column (1.0 mL/min carrier gas flow). Optical rotations were measured with a Jasco P-1010 polarimeter at 589 nm. $^1$H and $^{13}$C NMR spectra were recorded on a Varian Mercury 300 (at 300 MHz and 75 MHz respectively), and are reported relative to Me$_4$Si (δ 0.0). Data for $^1$H NMR spectra are reported as follows: chemical shift (δ ppm) (multiplicity, coupling constant (Hz), integration). Data for $^{13}$C NMR spectra are reported in terms of chemical shift relative to Me$_4$Si (δ 0.0). IR spectra were recorded on a Perkin Elmer Paragon 1000 spectrometer and are reported in frequency of absorption (cm$^{-1}$). High resolution mass spectra were obtained from the Caltech Mass Spectral Facility. Crystallographic data have been deposited at the CCDC, 12 Union Road, Cambridge CB2 1EZ, UK and copies can be obtained on request, free of charge, by quoting the publication citation and the deposition number.

General Procedure for the Asymmetric Allylation of Silyl Enol Ethers. A 50 mL round bottom flask equipped with a magnetic stir bar was flame dried under vacuum. After cooling under dry argon, catalyst (0.025 mmol, 0.025 equiv), chiral ligand (0.0625 mmol, 0.0625 equiv), and desilylating agent (0.35 mmol, 0.35 equiv) were added. After the flask was flushed with argon, solvent (30 mL) was added, the contents were stirred at 25° C. for 30 min, at which time the allylating agent (1.05 mmol, 1.05 equiv) and then the silyl enol ether substrate (1.0 mmol, 1.0 equiv) were added by syringe in one portion. When the reaction was complete by TLC, the reaction mixture evaporated under reduced pressure and the residue chromatographed (2→3% Et$_2$O in Pentane on SiO$_2$) to afford the product ketone.

EXAMPLE 1

TABLE 1

Ligand Screen in enantioselective allylation.

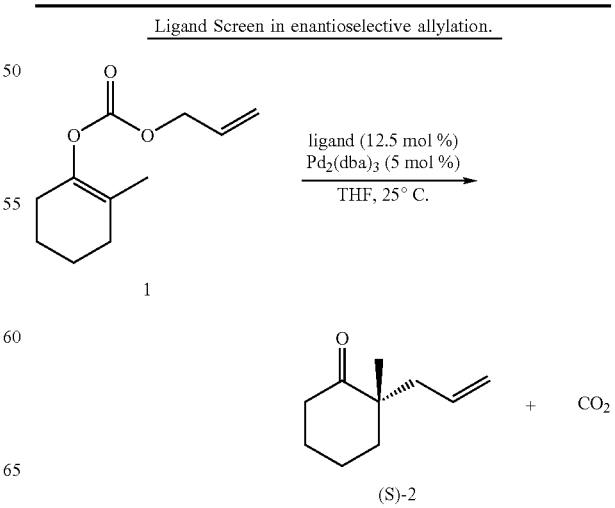

TABLE 1-continued

| Entry | Ligand | Time (h) | % yield[a] | % e.e.[b] |
|---|---|---|---|---|
| 1 | (R,R) - Trost Ligand (3) | 5 | 92 | 64[c] |
| 2 | (R)-BINAP (4) | 5 | 76 | 2[c] |
| 3 | (R,R)-Me-DUPHOS (5) | 5 | 66 | 0 |
| 4 | (R,R)-DIOP (6) | 2 | 59 | 2[c] |
| 5 | (R)-MOP (7) | 3 | 47 | 13 |
| 6 | (R)-QUINAP (8) | 2 | 97 | 61 |
| 7 | (R)-Ph-PHOX (9) | 2 | 95 | 65[c] |
| 8 | (S)-Bn-PHOX (10) | 5 | 94 | 63 |
| 9 | (R)-i-Pr-PHOX (11) | 2 | 95 | 83[c] |
| 10 | (S)-t-Bu-PHOX (12) | 2 | 96 | 88 |

[a]GC yield relative to an internal standard (tridecane).
[b]Enantiomeric excess (e.e.) measured by chiral GC.
[c](R)-2 produced as the major product.

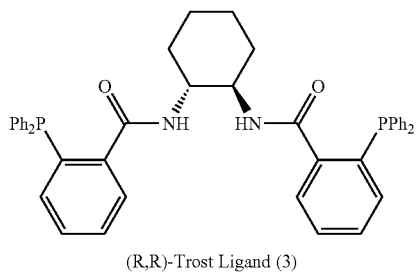

(R,R)-Trost Ligand (3)

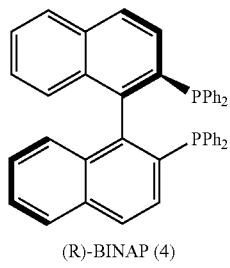

(R)-BINAP (4)

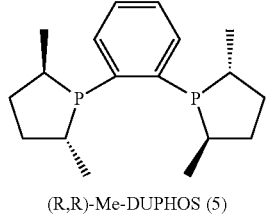

(R,R)-Me-DUPHOS (5)

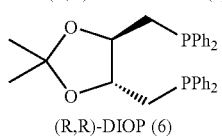

(R,R)-DIOP (6)

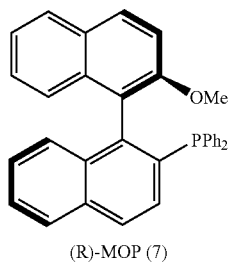

(R)-MOP (7)

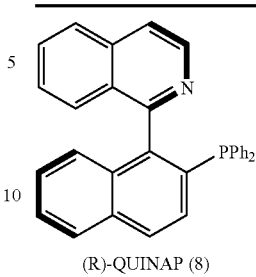

(R)-QUINAP (8)

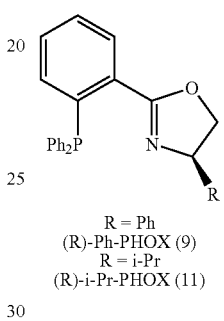

R = Ph
(R)-Ph-PHOX (9)
R = i-Pr
(R)-i-Pr-PHOX (11)

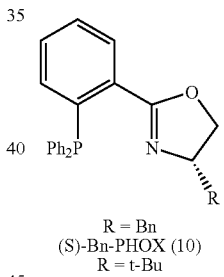

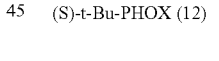

R = Bn
(S)-Bn-PHOX (10)
R = t-Bu
(S)-t-Bu-PHOX (12)

The reactions of Table 1 were conducted using the general procedure for the Asymmetric Allylation of Allyl Enol Carbonates, as follows.

General Procedure for the Asymmetric Allylation of Allyl Enol Carbonates. A 50 mL round bottom flask equipped with a magnetic stir bar was flame dried under vacuum. After cooling under dry argon, catalyst (0.025 mmol, 0.025 equiv) and chiral ligand (0.0625 mmol, 0.0625 equiv) were added. After the flask was flushed with argon, solvent (30 mL) was added and the contents were stirred at 25° C. for 30 min, at which time the allyl enol carbonate substrate (1.0 mmol, 1.0 equiv) was added by syringe in one portion. When the reaction was complete by TLC, the reaction mixture was evaporated under reduced pressure and the residue chromatographed (2→3% $Et_2O$ in Pentane on $SiO_2$) to afford the product ketone.

EXAMPLE 2

TABLE 2

Enantioselective Enol-Carbonate Allylation

| Entry | Substrate | Product | | Time [h] | Yield [%][a] | e.e. [%][b] |
|---|---|---|---|---|---|---|
| 1 | | | | 2 | 85 | 87 |
| 2[c] | | | | 5 | 85 | 88 (96)[d] |
| 3[e] | | | | 9 | 90 | 89 |
| 4 | | | R = CH$_2$CH$_3$ | 2 | 96 | 92 |
| 5[f] | | | R = t-Bu | 10 | 55[g] | 82 |
| 6 | | | R = CH$_2$Ph | 2 | 96 | 85 |
| 7 | | | R = (CH$_2$)$_3$OBn | 2 | 87 | 88 |
| 8[f] | | | | 8 | 89 | 91 |
| 9 | | | | 1 | 94 | 92 |
| 10 | | | | 1 | 87 | 86 |
| 11 | | | | 1 | 91 | 89 |
| 12[h] | | | R = H | 2 | 87 | 91 |
| 13[h] | | | R = OCH$_3$ | 8 | 94 | 91 |

TABLE 2-continued

Enantioselective Enol-Carbonate Allylation

| Entry | Substrate | Product | | Time [h] | Yield [%][a] | e.e. [%][b] |
|---|---|---|---|---|---|---|
| 14 | OCO₂allyl (cycloheptenyl carbonate) | allyl ketone | n = 1 | 6 | 81 | 87 |
| 15 | | | n = 2 | 2 | 90 | 79 |

[a]Isolated yields.
[b]Measured by chiral GC or HPLC.
[c]Performed on 5.1 mmol scale.
[d]In parentheses is the % e.e. after one recrystallization of the corresponding semicarbazone.
[e]Reaction performed at 12° C. (GC yield).
[f]Performed with 5 mol % $Pd_2(dba)_3$ and 12.5 mol % (S)-t-Bu-PHOX.
[g]Isolated yield after conversion to the corresponding diketone via Wacker oxidation.
[h]Performed at 10° C.

The reactions of Table 2 were performed using 1.0 mmol of substrate in THF (0.033 M in substrate) at 25° C. with $Pd_2(dba)_3$ (2.5 mol %), (S)-t-Bu-PHOX (6.25 mol %), unless stated otherwise.

EXAMPLE 3

The reactions of Table 3 were performed using 1.0 mmol of substrate in THF (0.033 M in substrate) at 25° C. with $Pd_2(dba)_3$ (2.5 mol %), (S)-t-Bu-PHOX (6.25 mol %), diallyl carbonate (1.05 equiv) as an allylating reagent, and TBAT (35 mol %) unless stated otherwise.

TABLE 3

Enantioselective Enol-Silane Allylation.

| Entry | Substrate | Product | | Time [h] | Yield [%][a] | e.e. [%][b] |
|---|---|---|---|---|---|---|
| 1 | OTMS cyclohexenyl-R | allyl ketone-R | R = CH₃ | 2 | 95 | 87 |
| 2 | | | R = CH₂CH₃ | 3 | 96 | 92 |
| 3[c] | OTMS (methyl cyclohexenyl) | methallyl ketone | | 4 | 79 | 91 |
| 4 | OTMS (dioxolane-fused) | allyl ketone (dioxolane) | | 2 | 99 | 81 |
| 5 | OTMS (methyl cycloalkenyl) | allyl ketone | n = 1 | 2 | 94 | 86 |
| 6 | | | n = 2 | 3 | 96 | 79 |

[a]Isolated Yields
[b]Measured by chiral GC or HPLC
[c]Reaction performed with dimethallyl carbonate (1.05 equiv)

Characterization Data for Products Listed in Table 3:

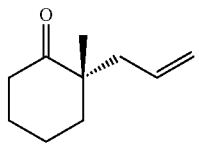

¹H NMR (300 MHz, CDCl₃) δ 5.75–5.61 (m, 1H), 5.05 (s, 1H), 5.01 (m, 1H), 2.40–2.31 (m, 3H), 2.21 (dd, J=13.8, 7.5 Hz, 1H), 1.78 (m, 5H), 1.56 (m, 1H), 1.06 (s, 3H); ¹³C NMR (75 MHz, CDCl₃) δ 215.4, 133.7, 117.9, 48.4, 41.9, 38.8, 38.5, 27.4, 22.6, 21.0; IR (Neat Film NaCl) 2934, 2865, 1707, 1451, 912 cm−1; HRMS m/z calc'd for $C_{10}H_{16}O$ [M]+: 152.1201. found 152.1204; [α]D28 −22.90° (c 2.09, hexane, 98% ee).

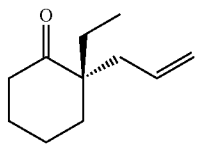

¹H NMR (300 MHz, CDCl₃) δ 5.66 (m, 1H), 5.02 (m, 2H), 2.47–2.18 (m, 4H), 1.90–1.60 (m, 7H), 1.46 (ddd, J=21.6, 15.0, 7.2 Hz, 1H), 0.75 (t, J=7.5 Hz, 3H); ¹³C NMR (75 MHz, CDCl₃) δ 215.0, 134.2, 117.6, 51.6, 39.2, 38.5, 36.0, 27.2, 27.1, 20.7, 7.8; IR (Neat Film NaCl) 2937, 1703 cm−1; HRMS m/z calc'd for $C_{11}H_{18}O$ [M]+: 166.1358. found 166.1362; [α]D28 +28.58° (c 1.51, hexane, 92% ee).

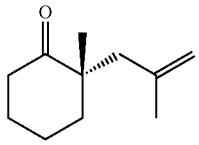

¹H NMR (300 MHz, CDCl₃) δ 4.81 (s, 1H), 4.64 (s, 1H), 2.52 (m, 1H), 2.48 (d, J=13.5 Hz, 1H), 2.36 (app. dt, J=14.7, 6.0 Hz, 1H), 2.25 (d, J=13.8 Hz, 1H), 1.94–1.53 (m, 6H), 1.65 (s, 3H), 1.06 (s, 3H); ¹³C NMR (75 MHz, CDCl₃) δ 215.8, 142.2, 114.7, 48.7, 45.4, 40.0, 38.9, 27.6, 24.3, 23.3, 21.1; IR (neat) 2927, 1707 cm−1; HRMS m/z calc'd for $C_{11}H_{18}O$[M]+: 166.1358. found 166.1358; [α]D27 −26.42° (c 1.85, hexane, 90% ee).

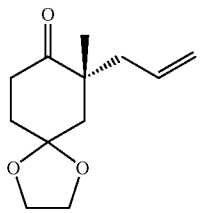

¹H NMR (300 MHz, CDCl₃) δ 5.67 (ddt, J=17.1, 10.5, 7.2 Hz, 1H), 5.07 (bs, 1H), 5.02 (app. d, J=9.3 Hz, 1H), 3.99 (app. d, J=1.5 Hz, 4H), 2.57 (app. t, J=6.3 Hz, 1H), 2.42 (m, 2H), 2.00 (d, J=13.8 Hz, 1H), 1.98 (app. t, J=7.2 Hz, 1H), 1.75 (d, J=14.1 Hz, 1H), 1.12 (s, 3H); ¹³C NMR (75 MHz, CDCl₃) δ 213.9, 133.7, 118.4, 107.6, 64.4, 64.3, 47.5, 44.3, 42.7, 35.7, 34.5, 23.9; IR (Neat Film NaCl) 2964, 1710, 1116 cm−1; HRMS m/z calc'd for $C_{12}H_{18}O_3$ [M]+: 210.1256. found 210.1255; [α]D29 −7.99° (c 2.41, hexane, 86% ee).

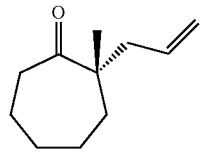

¹H NMR (300 MHz, CDCl₃) δ 5.70 (ddt, J=16.8, 10.2, 7.5, 1H), 5.02 (m, 2H), 2.59 (app. td, J=11.1, 2.7 Hz, 1H), 2.42 (app. t, J=9.0 Hz, 1H), 2.24 (dd, J=13.8, 7.5 Hz, 1H), 2.16 (dd, J=13.8, 7.8 Hz, 1H), 1.78–1.30 (m, 8H), 1.03 (s, 3H); ¹³C NMR (75 MHz, CHCl₃) δ 217.4, 133.8, 117.9, 50.8, 43.6, 40.6, 36.6, 30.6, 26.4, 24.4, 22.3; IR (Neat Film NaCl) 2930, 1702, 1458 cm−1; HRMS m/z calc'd for $C_{11}H_{18}O$ [M]+: 166.1358. found 166.1360; [α]D28 −34.70° (c 1.52, hexane, 87% ee).

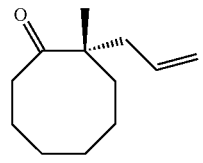

¹H NMR (300 MHz, CDCl₃) δ 5.67 (m, 1H), 5.04 (app. d, J=1.2 Hz, 1H), 5.00 (app. d, J=8.1 Hz, 1H), 2.59 (m, 1H), 2.29 (m, 2H), 2.12 (dd, J=14.1, 7.7 Hz, 1H), 2.01 (m, 1H), 1.83–1.70 (m, 3H), 1.61–1.32 (m, 5H), 1.18 (m, 1H), 1.01 (s, 3H); ¹³C NMR (75 MHz, CDCl₃) δ 220.3, 133.9, 117.8, 50.1, 42.0, 36.8, 33.5, 30.4, 25.9, 24.8, 24.3, 19.8; IR (Neat Film NaCl) 2929, 1699 cm−1; HRMS m/z calc'd for $C_{12}H_2O$ [M]+: 180.1514. found 180.1508; [α]D26 −21.22° (c 1.56, hexane, 79% ee).

EXAMPLE 4

TABLE 4

Catalytic enantioconvergent decarboxylative allylation of α-substituted 2-carboxyallyl cyclohexanones.

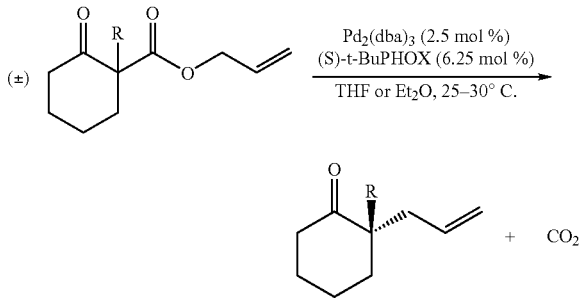

| Entry | R | Solvent | Temperature [° C.] | Time [h] | Yield [%]a | e.e. [%]b |
|---|---|---|---|---|---|---|
| 1 | CH₃ | THF | 25 | 7.5 | 85 | 88 |

TABLE 4-continued

| | | | | | | |
|---|---|---|---|---|---|---|
| 2 | $CH_3$ | $Et_2O$ | 25 | 4.75 | 89 | 88 |
| 3 | Prenyl | $Et_2O$ | 30 | 6 | 97 | 91 |
| 4 | $CH_2CH_2CN$ | $Et_2O$ | 25 | 6.5 | 97 | 88 |
| 5[c] | $CH_2CH_2CO_2Et$ | $Et_2O$ | 25 | 6 | 96 | 90 |
| 6 | $CH_2C_6H_5$ | THF | 25 | 0.5 | 99 | 85 |
| 7 | $CH_2(4-CH_3OC_6H_4)$ | THF | 25 | 10 | 80 | 86 |
| 8 | $CH_2(4-CF_3C_6H_4)$ | THF | 25 | 0.5 | 99 | 82 |
| 9[c] | $CH_2OSi(C_6H_5)_2C(CH_3)_3$ | THF | 25 | 5 | 86 | 81 |
| 10 | F | $Et_2O$ | 30 | 3.5 | 80 | 91 |

[a]Isolated yield from reaction of 1.0 mmol substrate at 0.033 M in solvent, unless otherwise noted.
[b]Enantiomeric excess (e.e.) determined by chiral GC or HPLC
[c]4 mol % $Pd_2(dba)_3$, 10 mol % (S)-t-BuPHOX, 0.021 M.

General procedure for the enantioconvergent allylation reactions of Table 4. Entry 1, Table 1: A 100 mL rb flask was equipped with a magnetic stir bar and flame dried under vacuum. After cooling under dry nitrogen, $Pd_2(dba)_3$ (22.9 mg, 0.025 mmol, 0.025 equiv) and (S)-t-BuPHOX (24.2 mg, 0.0625 mmol, 0.0625 equiv) were added. The flask containing the solids was evacuated for 15 min and then refilled with dry nitrogen. Dry THF (30 mL) was then added and the resulting solution stirred at 25° C. for 30 min. At this point, the substrate was added via syringe in one portion. When the reaction was complete by TLC, the reaction mixture was evaporated under reduced pressure and the residue purified by column chromatography ($SiO_2$, 1.5→2.5% $Et_2O$ in pentane) to afford the product α-allyl ketone.

EXAMPLE 5

TABLE 5

Enantioconvergent Decarboxylative Allylation of β-Ketoesters.[a]

| Entry | Substrate | Product | Temperature [° C.] | Time [h] | Yield [%][b] | e.e. [%][c] |
|---|---|---|---|---|---|---|
| 1 | | | 25 | 1.5 | 94 | 85 |
| 2[d] | | | 25 | 24 | 94 | 86 |
| 3 | | | 30 | 9 | 89 | 90 |
| 4 | | | 25 | 5 | 90 | 85 |
| 5[e,f] | | | 30 | 4 | 77 | 90 |
| 6[e] | | | 25 | 10 | 97 | 92 |
| 7 | | | 25 | 9.5 | 83 | 87 |

TABLE 5-continued

Enantioconvergent Decarboxylative Allylation of β-Ketoesters.[a]

| Entry | Substrate | Product | | Temperature [° C.] | Time [h] | Yield [%][b] | e.e. [%][c] |
|---|---|---|---|---|---|---|---|
| 8[e] | 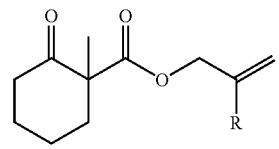 | 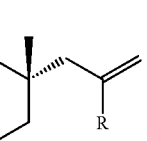 | R = CH₃ | 35 | 6.5 | 87 | 92 |
| 9[e,f] | | | R = Cl | 35 | 2.5 | 87 | 91 |
| 10 | 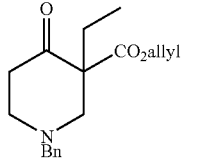 | 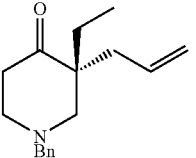 | | 25 | 2.5 | 91 | 92 |

[a]General reaction conditions and procedures are the same as for Example 4.
[b]Isolated yield from reaction of 1.0 mmol substrate, 2.5 mol % Pd$_2$(dba)$_3$, and 6.25 mol % (S)-t-BuPHOX at 0.033 M in THF, unless otherwise noted.
[c]Determined by chiral GC or HPLC.
[d]25 mmol substrate, 1.5 mol % Pd$_2$(dba)$_3$, and 3.75 mol % (S)-t-BuPHOX.
[e]Performed in Et$_2$O.
[f]4 mol % Pd$_2$(dba)$_3$, and 10 mol % (S)-t-BuPHOX, at 0.021 M.

EXAMPLE 6

TABLE 6

Decarboxylative allylation using Palladium(II) Catalyst.[a]

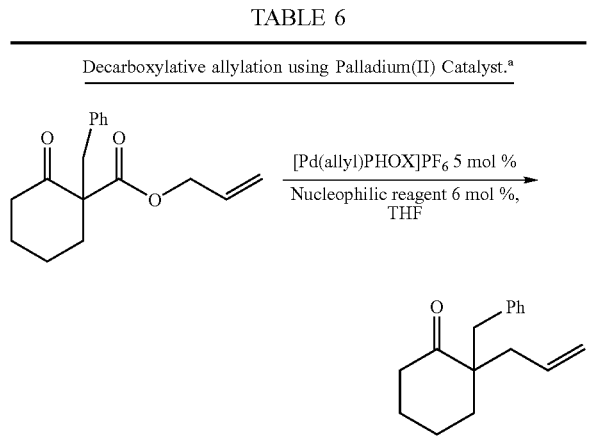

TABLE 6-continued

| Entry | Nucleophilic reagent | Yield [%] | e.e. [%] |
|---|---|---|---|
| 1 | NBu$_4$OH | 60–91 | 66.9–80.5 |
| 2 | TBAT | 70.0–78.0 | 73.0–80.0 |
| 3 | TBAF | 70.0–72.0 | 71.0–78.0 |
| 4 | NMe$_4$OH(H$_2$O)$_5$ | 72.0 | 77.8 |
| 5 | KOH, 18-crown-6 | 70.5–72.0 | 83.0–84.5 |
| 6 | 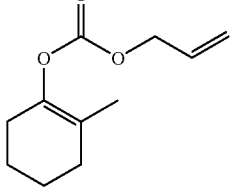, TBAT | 99 | 80 |

[a]General reaction conditions and procedures are the same as for Example 4.

EXAMPLE 7

TABLE 7

Decarboxylative Allylation using Various Catalysts[a]

| Entry | Substrate | Catalyst | Product | Time [hr] | Yield [%] | e.e. [%] |
|---|---|---|---|---|---|---|
| 1[b] | 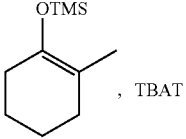 | Pd(cp)(η³-allyl) | 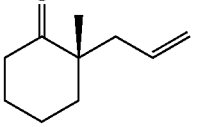 | 1 | 99 | 87.4 |

TABLE 7-continued

Decarboxylative Allylation using Various Catalysts[a]

| Entry | Substrate | Catalyst | Product | Time [hr] | Yield [%] | e.e. [%] |
|---|---|---|---|---|---|---|
| 2[c] | 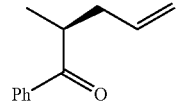 | ((S)-t-BuPHOX)PdCl$_2$ | 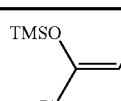 | 1 | 50 | 37.3 |
| 3[d] | 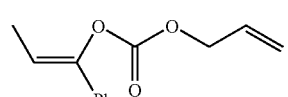 | Pd$_2$(dba)$_3$·CHCl$_3$ | | 4 | >95 | 87.2 |
| 4[e] | | Pd(OAc)$_2$ | | 6 | >95 | 87.5 |

[a]General procedure and reaction conditions are as follows (see Table 4 for procedural details): THF solvent, 25° C., (S)-t-BuPHOX ligand except where noted.
[b]Used 10 mol % catalyst, 12.5 mol % ligand.
[c]Used 5 mol % catalyst, and NaBH$_4$ was added to the reaction. No additional (S)-t-BuPHOX ligand was added.
[d]Used 3.5 mol % catalyst, 10 mol % ligand.
[e]Used 4 mol % catalyst, 8 mol % ligand.

EXAMPLE 8

TABLE 8

Allylations using Acyclic Substrates

Substrate → [Pd$_2$(dba)$_3$, (S)-t-BuPHOX, THF, 22° C.] → 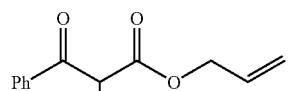

| Entry | Substrate | Time [hr] | Yield [%] | e.e. [%] |
|---|---|---|---|---|
| 1[a] | TMSO, Ph (vinyl) | 6–24 | 49 | 80 |
| 2 | allyl carbonate of enol Ph | 0.66 | 82 | 69 |
| 3 | Ph-C(O)-CH(Me)-C(O)-O-allyl | 4 | 31 | 63 |

[a]Added diallylcarbonate and 0.15 equivalents TBAT to the reaction.

EXAMPLE 9

ALLYLATIONS USING ACYCLIC SUBSTRATES

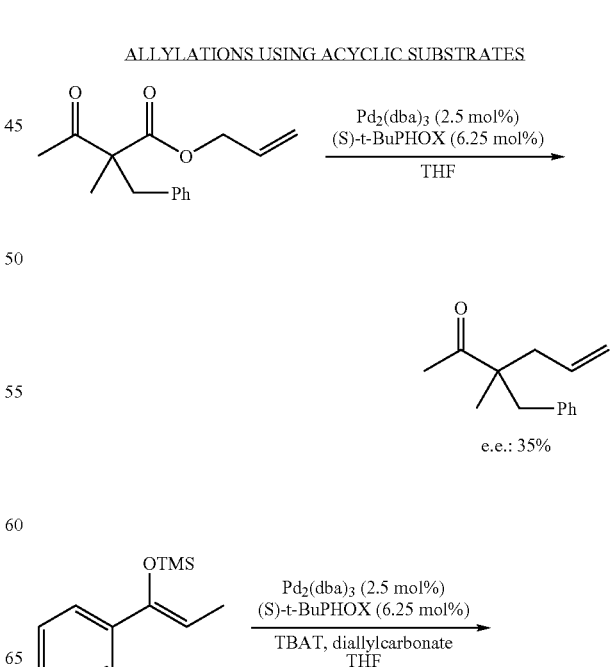

e.e.: 35%

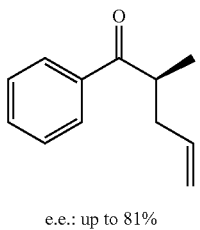

e.e.: up to 81%

EXAMPLE 10

TABLE 9

Allylations using Acyclic Substrates

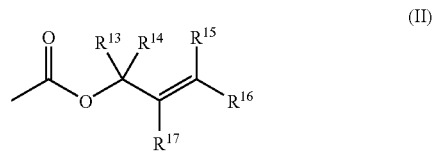

| Entry | E:Z ratio | Yield [%] | e.e. [%] |
|---|---|---|---|
| 1[a] | Pure Z | 82 | 68.8 |
| 2 | 1:3 | 79 | 64.9 |
| 3 | 1:2 | 82 | 65.1 |
| 4 | 1:1 | 82 | 65.3 |
| 5 | 3:1 | 66 | 66.0 |

[a]Reaction repeated at 10° C., 4 hr reaction time. Yield = 79%, e.e. = 71.5%.

EXAMPLE 11

General Procedure for the Synthesis of Silyl Enol Ethers

The following synthetic procedure yields the substrate of Table 3, entries 1 and 2. To a solution of sodium iodide (15.0 g, 100 mmol, 1.25 equiv) in MeCN (125 mL) were added 2-ethylcyclohexanone (10.1 g, 80 mmol, 1.0 equiv), TEA (14.0 mL, 100 mmol, 1.25 equiv), and finally TMSCl (11.6 mL, 91.2 mmol, 1.14 equiv) in a dropwise fashion. After 1 h, pentane (75 mL) was added, the biphasic mixture was stirred for 2 min, and the pentane decanted. After additional pentane extractions (5×75 mL), the combined pentane fractions were washed with water (2×50 mL), brine (1×50 mL), and dried ($Na_2SO_4$). Evaporation under reduced pressure gave the crude silyl enol ether (12.0 g) as an 80:20 mixture (NMR) of regioisomers favoring the tetrasubstituted silyl enol ether. An oxygen balloon was affixed to a flask containing a solution of the crude silyl enol ether (6.0 g) and palladium (II) diacetate (338.9 mg, 1.51 mmol) in DMSO (250 mL). The reaction mixture darkened and became heterogeneous. After 48 h, $^1$H NMR analysis of an aliquot indicated less than 2% of the undesired isomer, and the reaction mixture was poured into a separatory funnel containing pentane (300 mL), water (300 mL), and ice (200 g). The layers were separated and the aqueous layer extracted with pentane (3×200 mL). The pentane fractions were washed with water (2×100 mL), brine (100 mL), and dried ($Na_2SO_4$). Evaporation and chromatography (2% $Et_2O$ in Hexanes on $SiO_2$) afforded the pure silyl enol ether (3.21 g, 40.5% yield).

What is claimed is:

1. A method for synthesizing a compound containing a substituted or unsubstituted allyl group directly bound to a chiral carbon atom, comprising contacting an allyloxycarbonyl-substituted reactant with a transition metal catalyst in the presence of a chiral ligand, wherein the allyloxycarbonyl group is optionally substituted with one or more nonhydrogen substituents.

2. The method of claim 1, wherein the reactant is achiral.

3. The method of claim 1, wherein the reactant is chiral.

4. The method of claim 3, wherein the reactant comprises a racemic mixture of enantiomers.

5. The method of claim 1, wherein the method is enantioselective, such that the compound is provided in enantioenriched form.

6. The method of claim 1, wherein the optionally substituted allyloxycarbonyl group has the structure of formula (II)

$$\text{(II)}$$

wherein $R^{13}$, $R^{14}$, $R^{15}$, $R^{16}$ and $R^{17}$ are independently selected from H, hydrocarbyl, substituted hydrocarbyl, heteroatom-containing hydrocarbyl, substituted heteroatom-containing hydrocarbyl, and functional groups, and any two of $R^{13}$, $R^{14}$, $R^{15}$, $R^{16}$ and $R^{17}$, may be taken together and/or linked to another atom within the reactant to form a cyclic group.

7. The method of claim 1, wherein the reactant is an allyl enol carbonate.

8. The method of claim 1, wherein the reactant is a β-ketoester.

9. The method of claim 1, wherein the catalyst comprises a complex of a Group 6, 8, 9 or 10 transition metal.

10. The method of claim 9, wherein the transition metal is selected from Mo, W, Ir, Rh, Ru, Ni, Pt, and Pd.

11. The method of claim 10, wherein the transition metal is Pd.

12. The method of claim 11, wherein the catalyst comprises a complex of Pd(0).

13. The method of claim 12, wherein the catalyst is selected from: tris(dibenzylideneacetone)dipalladium(0); Pd(OC(0))CH$_3$)$_2$; PdCl$_2$(R$^{23}$CN)$_2$; PdCl$_2$(PR$^{24}$R$^{25}$R$^{26}$)$_2$; [pd($\eta_3$-allyl)Cl]$_2$; and Pd(PR$^{24}$R$^{25}$R$^{26}$)$_4$, wherein R$^{23}$, R$^{24}$, R$^{25}$ and R$^{26}$ are independently selected from H, hydrocarbyl, substituted hydrocarbyl, heteroatom-containing hydrocarbyl, and substituted heteroatom-containing hydrocarbyl.

14. The method of claim 13, wherein the catalyst is tris(dibenzylideneacetone)dipalladium(0).

15. The method of claim 11, wherein the catalyst comprises a complex of Pd(II).

16. The method of claim 15, wherein the Pd(II) catalyst is further reduced to Pd(0) in situ.

17. The method of claim 16, wherein catalyst is selected from allylchloro[1,3-bis(2,6-di-i-propylphenyl)imidazol-2-ylidene]palladium (II), ([2S,3S]-bis[diphenylphosphino]butane)($\eta_3$-allyl)palladium(II) perchlorate, [S]-4-tert-butyl-2-

(2-diphenylphosphanyl-phenyl)-4,5-dihydro-oxazole($\eta_3$-allyl)palladium(II) hexafluorophosphate, and cyclopentadienyl($\eta_3$-allyl)palladium(II).

18. The method of claim 16, wherein the catalyst is reduced with a reducing agent selected from $NBu_4OH$, $(n\text{-}Bu)_4N^+Ph_3SiF_2^-$, $(n\text{-}Bu)_4N^+F^-$, 4-dimethylaminopyridine, $NMe_4OH$ $(H_2O)_5$, $KOH/1,4,7,10,13,16$-Hexaoxacyclooctadecane, EtONa, and trimethyl-(2-methyl-cyclohex-1-enyloxy)-silane, or mixtures thereof.

19. The method of claim 1, wherein the chiral ligand is monodentate or bidentate, and is substantially enantiopure.

20. The method of claim 19, wherein the chiral ligand has the structure of formula (IV)

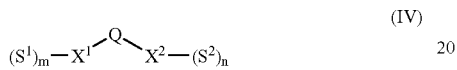

(IV)

wherein, in formula (IV),

Q is a linker selected from hydrocarbylene, substituted hydrocarbylene, heteroatom-containing hydrocarbylene, substituted heteroatom-containing hydrocarbylene, and a coordinated transition metal, and further wherein two or more substituents on Q may be linked to form a cycle;

$X^1$ and $X^2$ are independently selected from P, N, O, S, and As;

m and n are independently selected from 2, 3 and 4, and are chosen to satisfy the valency requirements of $X^1$ and $X^2$, respectively; and $S^1$ and $S^2$ are independently selected from hydrocarbyl, substituted hydrocarbyl, heteroatom-containing hydrocarbyl, and substituted heteroatom-containing hydrocarbyl, wherein two or more substituents on $S^1$ and/or $S^2$ may be linked to form a cycle, and further wherein $S^1$ and/or $S^2$ may form cycles such that $X^1$ and/or $X^2$ are incorporated into heterocycles.

21. The method of claim 20, wherein the chiral ligand is selected from oxazoles, phosphinooxazolines, imidazoles, phosphinoimidazolines, phosphines, phosphinopyridines, N-hetero carbenes, N-heterocyclic carbenes, and phosphinamines.

22. The method of claim 21, wherein the chiral ligand comprises an oxazolyl moiety.

23. The method of claim 22, wherein the chiral ligand is a phosphinooxazoline.

24. The method of claim 21, wherein the chiral ligand comprises a phosphinyl moiety.

25. The method of claim 24, wherein the chiral ligand is a bis-phosphine.

26. The method of claim 21, wherein the chiral ligand is an N-heterocyclic carbene.

27. The method of claim 21, wherein the chiral ligand is a phosphinamine.

28. The method of claim 19, wherein the chiral ligand has the structure of formula (V):

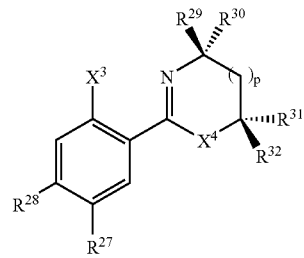

(V)

wherein, in formula (V):

$R^{27}$, $R^{28}$, $R^{29}$, $R^{30}$, $R^{31}$, and $R^{32}$ are independently selected from H, hydrocarbyl, substituted hydrocarbyl, heteroatom-containing hydrocarbyl, substituted heteroatom-containing hydrocarbyl, and functional groups, and any two of $R^{27}$, $R^{28}$, $R^{29}$, $R^{30}$, $R^{31}$, and $R^{32}$ on adjacent atoms may be taken together to form a cycle;

$X^3$ is selected from $-P(O)R^{33}R^{34}$, $-R^{33}R^{34}$, $-NR^{33}R^{34}$, $-OR^{33}$, $-SR^{33}$, and $-AsR^{33}R^{34}$, wherein $R^{33}$ and $R^{34}$ are independently selected from H, hydrocarbyl, substituted hydrocarbyl, heteroatom-containing hydrocarbyl, substituted heteroatom-containing hydrocarbyl, and functional groups;

$X^4$ is selected from $NR^{35}$ and O, wherein $R^{35}$ is selected from H, hydrocarbyl, substituted hydrocarbyl, heteroatom-containing hydrocarbyl, substituted heteroatom-containing hydrocarbyl, and functional groups; and p is 0 or 1.

29. The method of claim 1, wherein the contacting is carried out in a solvent at a temperature in the range of about 0° C. to about 100° C.

30. The method of claim 29, wherein the contacting is carried out at a temperature in the range of about 20° C. to about 25° C.

31. The method of claim 1, wherein the metal from the catalyst is present in an amount ranging from about 1 mol % to about 20 mol % relative to the reactant.

32. The method of claim 31, wherein the amount is from about 1 mol % to about 10 mol %.

33. The method of claim 1, wherein the chiral ligand is present in an amount ranging from about 1 mol % to about 20 mol % relative to the reactant.

34. The method of claim 33, wherein the amount is from about 6 mol % to about 13 mol %.

35. The method of claim 1, wherein the compound is an α-allyl ketone and is synthesized in at least 60% enantiomeric excess.

36. The method of claim 35, wherein the compound is synthesized in at least 85% enantiomeric excess.

37. A method for enantioselectively allylating an olefinic substrate, comprising contacting the substrate with an allylating reagent in the presence of a transition metal catalyst and a chiral ligand under reaction conditions effective to provide a compound containing a substituted or unsubstituted allyl group directly bound to a chiral carbon, wherein the substrate has the structure of formula (I)

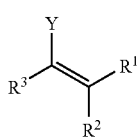

(I)

wherein, in formula (I):
R$^1$, R$^2$, and R$^3$ are independently selected from H, hydrocarbyl, substituted hydrocarbyl, heteroatom-containing hydrocarbyl, substituted heteroatom-containing hydrocarbyl, and functional groups, wherein any two of R$^1$, R$^2$, and R$^3$ may be taken together to form a cycle;
Y is selected from —OR$^4$, —NR$^5$R$^6$, and SR$^7$, in which:
R$^4$ is selected from SiR$^8$R$^9$R$^{10}$, SnR R$^9$R$^{10}$, and BR$^{11}$R$^{12}$, wherein R$^8$, R$^9$, and R$^{10}$ are independently selected from hydrocarbyl and substituted hydrocarbyl, R$^{11}$ and R$^{12}$ are independently selected from hydrocarbyl, substituted hydrocarbyl, heteroatom-containing hydrocarbyl, and substituted heteroatom-containing hydrocarbyl, and can optionally be taken together to form a cycle;
R$^5$ and R$^6$ are independently selected from Mg, Li, Zn, hydrocarbyl, substituted hydrocarbyl, heteroatom-containing hydrocarbyl, and substituted heteroatom-containing hydrocarbyl, and R$^5$ and R$^6$ can optionally be taken together to form a cycle; and
R$^7$ is hydrogen or hydrocarbyl.

38. The method of claim 37, wherein the allylating reagent comprises a substituted or unsubstituted allyl group.

39. The method of claim 38, wherein the allylating reagent contains an attached allylic group that has the structure of formula (III):

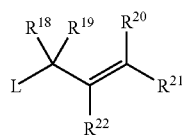

(III)

wherein L is a leaving group, and R$^{18}$, R$^{19}$, R$^{20}$, R$^{21}$ and R$^{22}$ are independently selected from H, hydrocarbyl, substituted hydrocarbyl, heteroatom-containing hydrocarbyl, substituted heteroatom-containing hydrocarbyl, and functional groups, and any two of R$^{18}$, R$^{19}$, R$^{20}$, R$^{21}$ and R$^{22}$ may be taken together and/or linked to another atom within the allylating reagent to form a cyclic group.

40. The method of claim 39, wherein the allylating reagent is an allyl carbonate.

41. The method of claim 40, wherein the allylating reagent is an allyl alkyl carbonate or an allyl aryl carbonate.

42. The method of claim 41, wherein the allylating reagent is selected from bis(allyl) carbonate, allyl methyl carbonate, allyl phenyl carbonate, allyl ethyl carbonate, allyl 1-benzotriazolyl carbonate, and allyl chlorophenyl carbonate.

43. The method of claim 39, wherein R$^{18}$, R$^{19}$, R$^{20}$, R$^{21}$ and R$^{22}$ are H.

44. The method of claim 39, wherein L is selected from halo, substituted or unsubstituted alkoxy, substituted or unsubstituted amido, substituted or unsubstituted carbamato, and substituted or unsubstituted carbonato.

45. The method of claim 44, wherein the allylating reagent is an allyl halide.

46. The method of claim 39, wherein the allylating reagent is a cycloalkene.

47. The method of claim 37, wherein Y is —OR$^9$, such that the olefinic substrate is an enol ether.

48. The method of claim 47, wherein R$^9$ is —SiR$^8$R$^9$R$^{10}$, such that the olefinic substrate is a silyl enol ether.

49. The method of claim 48, wherein the method further comprises a desilylating reagent in an amount effective to provide for desilylation of the olefinic substrate.

50. The method of claim 49, wherein the desilylating agent is selected from (n-Bu)$_4$N$^{+Ph}{}_3$SiF$_2{}^-$, MeLi, NaOEt, KOEt, KOtBu, CsF, and LiOMe.

51. The method of claim 47, wherein R$^9$ is SnR$^8$R$^9$R$^{10}$ such that the olefinic substrate is a stannyl enol ether.

52. The method of claim 47, wherein R$^9$ is BR$^{11}$R$^{12}$, such that the olefinic substrate is a boron enolate.

53. The method of claim 37, wherein Y is —NR$^5$R$^6$, such that the olefinic substrate is an enamine.

54. The method of claim 53, wherein the contacting results in the formation of an iminium ion.

55. The method of claim 54, further comprising hydrolyzing the iminium ion to form a ketone.

56. The method of claim 37, wherein the catalyst comprises a complex of a Group 6, 8, 9 or 10 transition metal.

57. The method of claim 56, wherein the transition metal is selected from Mo, W, Ir, Rh, Ru, Ni, Pt, and Pd.

58. The method of claim 57, wherein the transition metal is Pd.

59. The method of claim 58, wherein the catalyst comprises a complex of Pd(0).

60. The method of claim 59, wherein the catalyst is selected from: tris-(dibenzylideneacetone)dipalladium(0); Pd(OC(=O))CH$_3$)$_2$; PdCl$_2$(R$^{23}$CN)$_2$; PdCl$_2$(PR$^{24}$R$^{25}$R$^{26}$)$_2$; [Pd($\eta_3$-allyl)Cl]$_2$; and Pd(PR$^{24}$R$^{25}$R$^{26}$)$_4$, wherein R$^{23}$, R$^{24}$, R$^{25}$, and R$^{26}$ are independently selected from H, hydrocarbyl, substituted hydrocarbyl, heteroatom-containing hydrocarbyl, and substituted heteroatom-containing hydrocarbyl.

61. The method of claim 60, wherein the catalyst is tris(dibenzylideneacetone)dipalladium(0).

62. The method of claim 58, wherein the catalyst comprises a complex of Pd(II).

63. The method of claim 62, wherein the Pd(II) catalyst is further reduced to Pd(0) in situ.

64. The method of claim 63, wherein catalyst is selected from allylchloro[1,3-bis(2,6-di-i-propylphenyl)imidazol-2-ylidene]palladium (II), ([2S,3S]-bis[diphenylphosphino]butane)(Θ$_3$-allyl)palladium(II) perchlorate, [S]-4-tert-butyl-2-(2-diphenylphosphanyl-phenyl)-4,5-dihydro-oxazole($\eta_3$-allyl)palladium(II) hexafluorophosphate, and cyclopentadienyl($\eta_3$-allyl) palladium(II).

65. The method of claim 63, wherein the catalyst is reduced with a reducing agent selected from NBu$_4$tOH, (n-Bu)$_4$N$^+$Ph$_3$SiF$^-$, (n-Bu)$_4$N$^+$F$^-$, 4-dimethylaminopyridine, NMe$_4$OH (H$_2$O)$_5$, KOH/1,4,7,10,13,16-Hexaoxacyclooctadecane, EtONa, and trimethyl-(2-methyl-cyclohex-1-enyloxy)-silane, or mixtures thereof.

66. The method of claim 37, wherein the chiral ligand is monodentate or bidentate, and is substantially enantiopure.

67. The method of claim 66, wherein the chiral ligand has the structure of formula (IV)

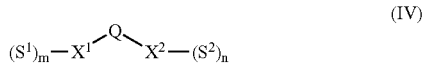

(IV)

wherein, in formula (IV),
Q is a linker selected from hydrocarbylene, substituted hydrocarbylene, heteroatom-containing hydrocarbylene, substituted heteroatom-containing hydrocarbylene, and a coordinated transition metal, and further wherein two or more substituents on Q may be linked to form a cycle;
$X^1$ and $X^2$ are independently selected from P, N, O, S, and As;
m and n are independently selected from 2, 3 and 4, and are chosen to satisfy the valency requirements of $X^1$ and $X^2$, respectively; and
$S^1$ and $S^2$ are independently selected from hydrocarbyl, substituted hydrocarbyl, heteroatom-containing hydrocarbyl, and substituted heteroatom-containing hydrocarbyl, wherein two or more substituents on $S^1$ and/or $S^2$ may be linked to form a cycle, and further wherein $S^1$ and/or $S^2$ may form cycles such that $X^1$ and/or $X^2$ are incorporated into heterocycles.

68. The method of claim 67, wherein the chiral ligand is selected from oxazoles, phosphinooxazolines, imidazoles, phosphinoimidazolines, phosphines, phosphinopyridines, N-heterocarbenes, N-heterocyclic carbenes, and phosphinamines.

69. The method of claim 68, wherein the chiral ligand comprises an oxazolyl moiety.

70. The method of claim 69, wherein the chiral ligand is a phosphinooxazoline.

71. The method of claim 68, wherein the chiral ligand comprises a phosphinyl moiety.

72. The method of claim 71, wherein the chiral ligand is a bis-phosphine.

73. The method of claim 68, wherein the chiral ligand is an N-heterocyclic carbene.

74. The method of claim 68, wherein the chiral ligand is a phosphinamine.

75. The method of claim 66, wherein the chiral ligand has the structure of formula (V)

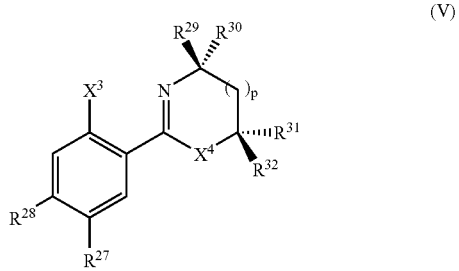

(V)

wherein, in formula (V):
$R^{27}$, $R^{28}$, $R^{29}$, $R^{30}$, $R^{31}$, and $R^{32}$ are independently selected from H, hydrocarbyl, substituted hydrocarbyl, heteroatom-containing hydrocarbyl, substituted heteroatom-containing hydrocarbyl, and functional groups, and any two of $R^{27}$, $R^{28}$, $R^{29}$, $R^{30}$, $R^{31}$, and $R^{32}$ on adjacent atoms may be taken together to form a cycle;
$X^3$ is selected from —P(O)$R^{33}R^{34}$, —P$R^{33}R^{34}$, —N$R^{33}R^{34}$, —O$R^{33}$, —S$R^{33}$, and —As$R^{33}R^{34}$, wherein $R^{33}$ and $R^{34}$ are independently selected from H, hydrocarbyl, substituted hydrocarbyl, heteroatom-containing hydrocarbyl, substituted heteroatom-containing hydrocarbyl, and functional groups;
$X^4$ is selected from N$R^{35}$ and O, wherein $R^{35}$ is selected from H, hydrocarbyl, substituted hydrocarbyl, heteroatom-containing hydrocarbyl, substituted heteroatom-containing hydrocarbyl, and functional groups; and
p is 0 or 1.

76. The method of claim 37, wherein the contacting is carried out in a solvent at a temperature in the range of about 0° C. to about 100° C.

77. The method of claim 76, wherein the contacting is carried out at a temperature in the range of about 20° C. to about 25° C.

78. The method of claim 37, wherein the metal from the catalyst is present in an amount ranging from about 1 mol % to about 20 mol % relative to the substrate.

79. The method of claim 78, wherein the amount is from about 1 mol % to about 10 mol %.

80. The method of claim 37, wherein the chiral ligand is present in an amount ranging from about 1 mol % to about 20 mol % relative to the substrate.

81. The method of claim 80, wherein the amount is from about 6 mol % to about 13 mol %.

82. The method of claim 37, wherein the compound is an α-allyl ketone and is provided in at least 60% enantiomeric excess.

83. The method of claim 82, wherein the compound is provided in at least 85% enantiomeric excess.

84. A method for catalytically and enantioconvergently synthesizing a compound, comprising contacting a mixture of isomers of a starting compound with a transition metal catalyst in the presence of a chiral ligand under reaction conditions sufficient to provide formation of a compound containing a carbon stereocenter, wherein the starting compound comprises a quaternary carbon stereocenter.

85. The method of claim 84 wherein the mixture consists essentially of stereo isomers of a β-ketoester.

* * * * *